(12) United States Patent
Seino et al.

(10) Patent No.: US 7,115,797 B2
(45) Date of Patent: Oct. 3, 2006

(54) MICE LACKING INWARD-RECTIFYING POTASSIUM CHANNEL KIR6.1

(75) Inventors: Susumu Seino, 1260-12, Aoba-cho, Chuo-ku, Chiba-shi 260-0852 (JP); Takashi Miki, Chiba (JP); Haruaki Nakaya, Chiba (JP)

(73) Assignees: JCR Pharmaceuticals Co., Ltd., Ashiya (JP); Susumu Seino, Chiba (JP)

( * ) Notice: Subject to any disclaimer, the term of this patent is extended or adjusted under 35 U.S.C. 154(b) by 408 days.

(21) Appl. No.: 10/388,005

(22) Filed: Mar. 14, 2003

(65) Prior Publication Data

US 2004/0098757 A1    May 20, 2004

(30) Foreign Application Priority Data

Mar. 19, 2002  (JP)  ............................. 2002-076170

(51) Int. Cl.
 *A01K 67/027*  (2006.01)
(52) U.S. Cl. ...................................................... 800/18
(58) Field of Classification Search .................. 800/18
See application file for complete search history.

(56) References Cited

OTHER PUBLICATIONS

Miki T, The structure and function of the ATP-sensitve potassium channel in insulin-secreting pancreatic beta-cells, 1999, J of Mol. Endocrinology, vol. 22, pp. 113-123.*
Kubo Y, Primary structure and functional expression of a mouse inward rectifier postassium channel, 1993, Nature, vol. 362, pp. 127-133.*
Capecchi MR, Targeted Gene Replacement, 1994, Scientific American, vol. 270, pp. 34-41.*
Lily Yeh Jan et al., "Annual Review Prize Lecture: Voltage-gated and Inwardly Rectifying Potassium Channels", Journal of Physiology, vol. 505, No. 2, pp. 267-282 (1997).
C.G. Nichols et al., "Inward Rectifier Potassium Channels", Annu. Rev. Physiol., vol. 59, pp. 171-191 (1997).
M. Roselle Abraham et al., Channelopathies of Inwardly Rectifying Potassium Channels, The FASEB Journal, vol. 13, pp. 1901-1910 (1999).
Frances M. Ashcroft et al., "Correlating Structure and Function in ATP-Sensitive K$^+$ Channels", TINS, vol. 21, No. 7, pp. 288-294 (1998).
Lydia Aguilar-Bryan et al., "Molecular Biology of Adenosine Triphosphate-Sensitive Potassium Channels", Endocrine Reviews, vol. 20, No. 2, pp. 101-135 (1999).
Susumu Seino, "ATP-Sensitive Potassium Channels: A Model of Heteromultimeric Potassium Channel/Receptor Assemblies", Annu. Rev. Physiol., vol. 61, pp. 337-367 (1999).
Nobuya Inagaki et al., "A Family of Sulfonylurea Receptors Determines the Pharmacological Properties of ATP-Sensitive K$^+$ Channels", Neuron, vol. 16, pp. 1011-1017 (1996).
Shojiro Isomoto et al., "Communication: A Novel Sulfonylurea Receptor Forms with BIR (Kir6.2) a Smooth Muscle Type ATP-Sensitive K$^+$ Channel", The Journal of Biological Chemistry, vol. 271, No. 40, pp. 24321-24324 (1996).

Nobuya Inagaki et al., "Research Articles: Reconstitution of $I_{KATP}$: An Inward Rectifier Subunit Plus the Sulfonylurea Receptor", Science, vol. 270, pp. 1166-1170 (1995).
Takashi Miki et al., "ATP-Sensitive K$^+$ Channels in the Hypothalamus are Essential for the Maintenance of Glucose Homeostasis", Nature Neuroscience, vol. 4, No. 5, pp. 507-512 (2001).
Takashi Miki et al., "Defective Insulin Secretion and Enhanced Insulin Action in $K_{ATP}$ Channel-Deficient Mice", Proc. Natl. Acad. Sci. USA, vol. 95, pp. 10402-10406 (1998).
Victor Seghers et al., "*Sur 1* Knockout Mice: A Model for $K_{ATP}$ Channel-Independent Regulation of Insulin Secretion", The Journal of Biological Chemistry, vol. 275, No. 13, pp. 9270-9277 (2000).
Masashi Suzuki et al., "Functional Roles of Cardiac and Vascular ATP-Sensitive Potassium Channels Clarified by Kir6.2-) Knockout Mice", Circulation Research, vol. 88, pp. 570-577 (2001).
Garrett J Gross et al., "Sarcolemmal Versus Mitochondrial ATP-Sensitive K$^+$ Channels and Myocardial Preconditioning", Circulation Research, vol. 84, pp. 973-979 (1999).
William A. Chutkow et al., "Disruption of *Sur2*-Containing $K_{ATP}$ Channels Enhances Insulin-Stimulated Glucose Uptake in Skeletal Muscle", PNAS, vol. 98, No. 20, pp. 11760-11764 (2001).
Carina Ämmälä et al., "The Sulphonylurea Receptor Confers Diazoxide Sensitivity on the Inwardly Rectifying K$^+$ channel Kir6.1 Expressed in Human Embryonic Kidney Cells", Journal of Physiology, vol. 494, No. 3, pp. 709-714 (1996).
Yongge Liu et al., Pharmacological Comparison of Native Mitochondrial $K_{ATP}$ Channels with Molecularly Defined Surface $K_{ATP}$ Channels, Molecular Pharmacology, vol. 59, No. 2, pp. 225-530 (2001).
Yutaka Kono et al., "the Properties of the Kir6.1-6.2 Tandem Channel Co-expressed with SUR2A", Pflugers. Arch.—Eur. J. Physiol., vol. 440, pp. 692-698 (2000).
Mitsuhiko Yamada et al., "Sulphonylurea Receptor 2B and Kir6.1 form a Sulphonylurea-Sensitive but ATP-Insensitive K$^+$ Channel", Journal of Physiology, vol. 499, No. 3, pp. 715-720 (1997).
Henrik Dörschner et al., "Stoichiometry of Sulfonylurea-Induced ATP-Sensitive Potassium Channel Closure", Molecular Pharmacology, vol. 55, pp. 1060-1066 (1999).
Annette Hambrock et al., "Characterization of a Mutant Sulfonylurea Receptor SUR2B with High Affinity for Sulfonylureas and Openers: Differences in the Coupling to Kir6.$\chi$ Subtypes", Mol. Pharmacology, vol. 60, pp. 190-199 (2001).

(Continued)

Primary Examiner—Dave Trong Nguyen
Assistant Examiner—David A. Montanari
(74) Attorney, Agent, or Firm—Greenblum & Bernstein, P.L.C.

(57) ABSTRACT

Mice homozygous for the lack of inward-rectifying potassium channel Kir6.1 gene are disclosed. The mice causes a high incidence of sudden death associated with arrhythmia (atrioventricular block) caused by spontaneous cardiac ischemia, a condition similar to Prinzmetal angina (variant angina) in human, representing an animal model of Prinzmetal angina. Mice heterozygous for the lack of inward-rectifying potassium channel Kir6.1 gene are also disclosed, which are used as parent mice for reproduction of the homozygous mice.

1 Claim, 10 Drawing Sheets

OTHER PUBLICATIONS

Myron Prinzmetal et al., "Angina Pectoris: I. A Variant Form of Angina Pectoris", American Journal of Medicine, vol. 27, pp. 375-388 (Sep. 1959).

Attilio Maseri, "Louis F. Bishop Lecture: Role of Coronary Artery Spasm n Symptomatic and Silent Myocardial Ischemia", JACC, vol. 9, No. 2, pp. 249-262 (1987).

Nihan Erginel-Unaltuna et al., "Genomic Organization and Expression of KCNJ8/Kir6.1, A Gene Encoding A Subunit of an ATP-Sensitive Potassium Channel[1]", Gene, vol. 211, pp. 71-78 (1998).

Michael Mederos y Schnitzler et al., "ATP-Sensitive Potassium Channels in Capillaries Isolated form Guinea-Pig Heart", Journal of Physiology, vol. 525, No. 2, pp. 307-317 (2000).

Kensuke Egashira et al., "Mechanism of Ergonovine-Induced Hyperconstriction of the Large Epicardial Coronary Artery in Conscious Dogs a Month After Arterial Injury", Circulation Research, vol. 71, No. 2, pp. 435-442 (1992).

Nobuya Inagaki et al., "Communication: Cloning and Functional Characterization of a Novel ATP-Sensitive Potassium of Channel Ubiquitously Expressed in Rat Tissues, Including Pancreatic Islets, Pituitary, Skeletal Muscle, and Heart", The Journal Biological Chemistry, vol. 270, No. 11, pp. 5691-5694 (1995).

D.J. Beech et al., "K Channel Activation by Nucleotide Diphosphates and its Inhibition by Glibenclamide in Vascular Smooth Muscle Cells", Br. J. Pharmacol., vol. 110, pp. 573-582 (1993).

Nicholas B. Standen et al., "Hyperpolarizing Vasodilators Activate ATP-Sensitive $K^+$ Channels in Arterial Smooth Muscle", Science, vol. 245, pp. 177-180 (1989).

Robert J. Myerburg et al., "Frequency of Sudden Cardiac Death and Profiles of Risk", Am J. Cardiol., vol. 80, No. 5B, pp. 10F-19F (1997).

Mark T. Keating et al., "Molecular and Cellular Mechanisms of Cardiac Arrhythmias", Cell, vol. 104, pp. 569-580 (2001).

David E. Gutstein et al., "Conduction Slowing and Sudden Arrhythmic Death in Mice With Cardiac-Restricted Inactivation of Connexin43", Circulation Research, vol. 88, pp. 333-339 (2001).

Jeffrey Robbins et al., "Listening for Hoof Beats in Heart Beats", Nature Medicine, vol. 6, No. 9, pp. 968-970 (2000).

Sabina Kupershmidt et al., "Replacement by Homologous Recombination of the *minK* Gene With *lacZ* Reveals Restriction of *minK* Expression to the Mouse Cardiac Conduction System", Circulation Research, vol. 84, pp. 146-152 (1999).

Milou-Daniel Drici et al., "Involvement of IsK-Associated $K^+$ Channel in Heart Rate Control of Repolarization in a Murine Engineered Model of Jervell and Lange-Nielsen Syndrome", Circ Res., vol. 83, pp. 95-102 (1998).

Dianne M. Barry et al., "Functional Knockout of the Transient Outward Current, Long-QT Syndrome, and Cardiac Remodeling in Mice Expressing a Dominant-Negative Kv4 α Subunit", Circ Res., vol. 83, pp. 560-567 (1998).

Ken Okumura et al., "Diffuse Disorder of Coronary Artery Vasomotility in Patients with Coronary Spastic Angina: 45-52 Hyperreactivity to the Constrictor Effects of Acetylcholine and the Dilator Effects of Nitroglycerin", JACC, vol. 27, No. 1, pp. (1996).

Rex N. Macalpin, "Cardiac Arrest and Sudden Unexpected Death in Variant Angina: Complications of Coronary Spasm that can Occur in the Absence of Severe Organic Coronary Stenosis", American Heart Journal, vol. 125, No. 4, pp. 1011-1017 (1993).

\* cited by examiner

MICE LACKING INWARD-RECTIFYING POTASSIUM CHANNEL KIR6.1

FIELD OF THE INVENTION

The present invention relates to mice lacking inward-rectifying potassium ($K^+$) channel Kir6.1 and serving as model animals of Prinzmetal angina (variant angine or vasospastic angina) in human.

BACKGROUND OF THE INVENTION

Inward-rectifying potassium channels (Kir) are playing a number of physiologically important roles (1). Based on their mutual sequence similarity, the Kir family is currently divided into seven subfamilies, Kir1.x–Kir7.x (1–3, 27). Unlike the other members of the Kir family, the members of Kir6.x subfamily, including Kir6.1 and Kir6.2, are unique in that they cannot form functional $K^+$ channels by themselves on the surface of cell membranes and that they require a regulatory SUR subunit) (4–6), which is the receptor for sulfonylurea compounds widely used for the treatment of Type II diabetes mellitus (noninsulin-dependent diabetes mellitus). The sulfonylurea receptor has two isoforms, SUR1 and SUR2 (7), derived from two different genes (7). In addition, there are several splicing variants of SUR2, among which major ones are SUR2A (7) and SUR2B (8). Co-expression of Kir6.2 subunit with SUR1, SUR2A or SUR2B or one of other SUR2 variant subunits produces $K_{ATP}$ channel currents with distinct nucleotide and pharmacological sensitivities in heterologous expression systems (4–6). The Kir6.2 subunit and the SUR1 subunit constitute the $K_{ATP}$ channel in pancreatic β-cells (9) and in the glucose-responsive neurons (GRNs) in ventromedial hypothalamus (VMH) (10). The Kir6.2 subunit and the SUR2A subunit constitute $K_{ATP}$ channels in cardiomyocytes and probably also in skeletal muscle cells (7). The Kir6.1 subunit and the SUR2B subunit constitute $K_{ATP}$ channels in non-vascular smooth muscles (8). Studies of Kir6.2 knockout mice have clarified a variety of physiological roles of Kir6.2-containing $K_{ATP}$ channels. For example, the Kir6.2/SUR1 channels in pancreatic β-cells are critical in both glucose-induced and sulfonylurea insulin secretion (11), while in VMH, Kir 6.2/SUR1 channels are involved in glucagon secretion during hypoglycemia (10) through autonomic neurons. Studies of SUR1 knockout mice confirm the importance of Kir6.2/SUR1 channels in insulin secretion (12). Kir6.2/SUR2A channels mediate the depression of cardiac excitability and contractility induced by $K^+$ channel openers (KCOs) (13), and contribute in part to ischemic preconditioning (14). In addition, in studies of SUR2 knockout mice, Kir6.2-containing $K_{ATP}$ channels in skeletal muscle have been shown to be involved in glucose uptake (15). While Kir6.1 subunits and SUR1 (16, 17), SUR2A (18), or SUR2B (19–21) subunits have been shown to generate $K^+$-channel currents with different electrophysiological and pharmacological properties, the actual combinations of Kir6.1 and SUR subunits naturally occurring in tissues, as well as their physiological roles, have not been determined.

Kir6.1 (its amino acid sequence is set forth as SEQ ID NO:1) shares 63.7% amino acid identity with its isoform Kir6.2. In addition, while inward-rectifier $K^+$ channels generally have the Gly-Tyr-Gly motif in their ion permeable region (H5), both Kir6.1 and Kir6.2 have the Gly-Phe-Gly motif in the region (6). Thus, Kir6.1 and Kir6.2 are structurally very similar. While the electrophysiological and pharmacological properties of Kir6.2-containing $K^+$ channels have been well characterized in reconstituted systems (7–9) and native cells (10, 11, 13), those of Kir6.1-containing $K^+$ channels are not fully understood. Co-expression of Kir6.1 and SUR1 in HEK293 cells produces tolbutamide-sensitive $K^+$ channel currents (16), and co-expression of Kir6.1 and SUR2A in COS7 cells produces currents that are responsive to very high concentrations of UDP (18). Their physiological significance, however, is not known. Co-expression of Kir6.1 and SUR2B, which is a splice variant of SUR2A in HEK293T cells, produces a $K^+$ current which is insensitive to ATP, activated by nucleoside diphosphates such as UDP, and inhibited by sulfonylurea glibenclamide (19). These properties are similar with those of $K_{NDP}$ channels in native vascular smooth muscle (28). The $K_{NDP}$ channel in vascular smooth muscle was originally called the smooth muscle $K_{ATP}$ channel as it is closed by glibenclamide (29), a $K_{ATP}$ channel blocker, but it has become designated as $K_{NDP}$ channel because of its insensitivity to ATP (28). Since the $K_{NDP}$ channels are opened by $K^+$ channel openers having vasodilating effects, such as cromakalim and pinacidil, the channels are thought to be involved in the vasodilatation response of vascular smooth muscles. However, it is unknown whether Kir6.1 is a component of the $K_{NDP}$ channels in native vascular smooth muscle.

On the other hand, there is a type of human angina pectoris called Prinzmetal angina (also called variant angina or vasospastic angina), which is accompanied by a reversible, tentative of ST elevation during angina attacks in the resting state. Attacks of Prinzmetal angina occurs in the resting state, especially from the night to early morning while one is sleeping. It is characterized by ST segment elevation on electrocardiogram upon attack with a lead which generally should record lowered ST segment in a typical angina pectoris, and it often shows arrhythmia such as ventricular extrasystole, atrioventricular block, ventricular fibrillation, etc. The attack is considered to be caused by sharp decrease of the coronary blood flow due to a spasm of a thick coronary artery.

SUMMARY OF THE INVENTION

The objective of the present invention is to provide model animals useful as means for elucidating physiological role of Kir6.1-containing $K^+$ channel and also for searching agents for treatment of diseases associated with dysfunctioning of Kir6.1, in particular Prinzmetal angina.

The present inventors generated mice homozygous for lack of Kir6.1 gene (Kir6.1$^{-/-}$ mice) by disrupting the gene using the gene targeting technique. Further, using the mice expressing no Kir6.1 gene product, the inventors also found that the Kir6.1-containing channel is critical in the regulation of vascular tonus, and that its genetic disruption in mice causes a high incidence of sudden death associated with arrhythmia (atrioventricular block) caused by spontaneous cardiac ischemia, a condition similar to Prinzmetal angina (variant angina) in human.

Thus, the present invention provides mice homozygous for the lack of inward-rectifying potassium channel Kir6.1 gene (Kir6.1$^{-/-}$ mice). The homozygous mice can be used for elucidation of the mechanism of development of Prinzmetal angina, as well as for screening of agents for its treatment.

The present invention further provides mice heterozygous for the lack of inward-rectifying potassium channel Kir6.1 gene (Kir6.1$^{+/-}$ mice). The heterozygous mice can be used as parent mice for reproduction of the above-identified homozygous mice, by crossing them with one another and then sorting the offspring.

The present invention further provides organs such as the heart and the like and tissues, in particular myocardial tissue and vascular tissues such as vascular smooth muscle tissue of the aorta and the like, as well as cells such as cardiac cells, vascular smooth muscle cells and the like. These tissues, organs and cells can be used for screening of agents for the treatment of Prinzmetal angina and other diseases associated with the abnormality of Kir6.1.

As mentioned later, K$^+$ channel opener pinacidil did not induce K$^+$ currents in vascular smooth muscle cells of Kir6.1$^{-/-}$ mice, and the Kir6.1$^{-/-}$ mice lacked vasodilation response to pinacidil. Administration of methylergometrine, a vasoconstrictive agent, induced ST elevation followed by cardiac death in Kir6.1$^{-/-}$ mice, but not in wild type (Kir6.1$^{+/+}$) mice. This indicates that Kir6.1$^{-/-}$ mice bear a phenotype resembling Prinzmetal angina in human characterized by hypercontractility of coronary arteries. These results indicates that Kir6.1-containing K$^+$ channel is critical in the regulation of vascular tonus, especially in the coronary arteries, and its disruption is involved in Prinzmetal angina.

NE=norepinephrine. The numbers 0.3, 1, 3 and 10 indicate the concentration (μM) of pinacidil applied.

Figure 13:
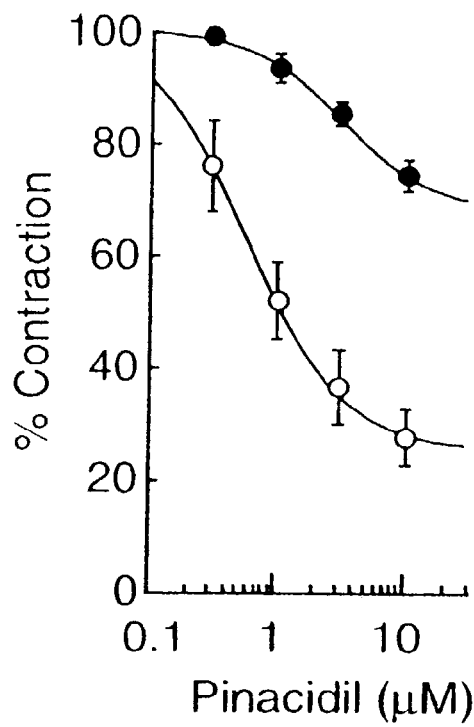

FIG. 13 is a graph showing dose (pinacidil)-response (dilation) relationship in aortic rings from Kir6.1$^{+/+}$ mice (○) and Kir6.1$^{-/-}$ mice (●).

Figure 14:
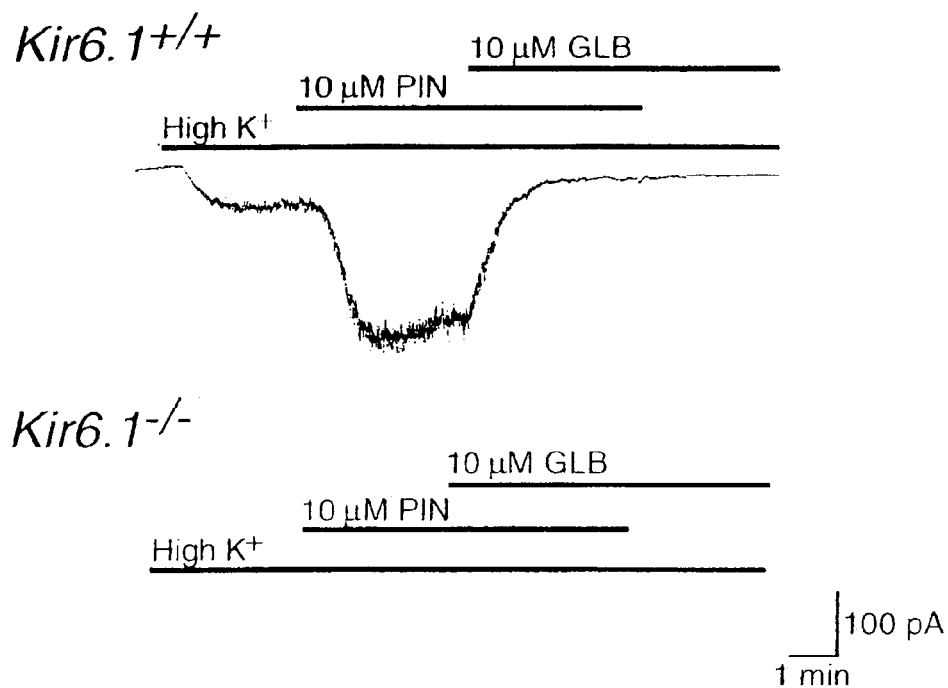

FIG. 14 shows recordings of pinacidil-induced, glibenclamide-sensitive currents in aortic smooth muscles of Kir6.1$^{+/+}$ mice (upper) and Kir6.1$^{-/-}$ mice (lower).

Figure 15:
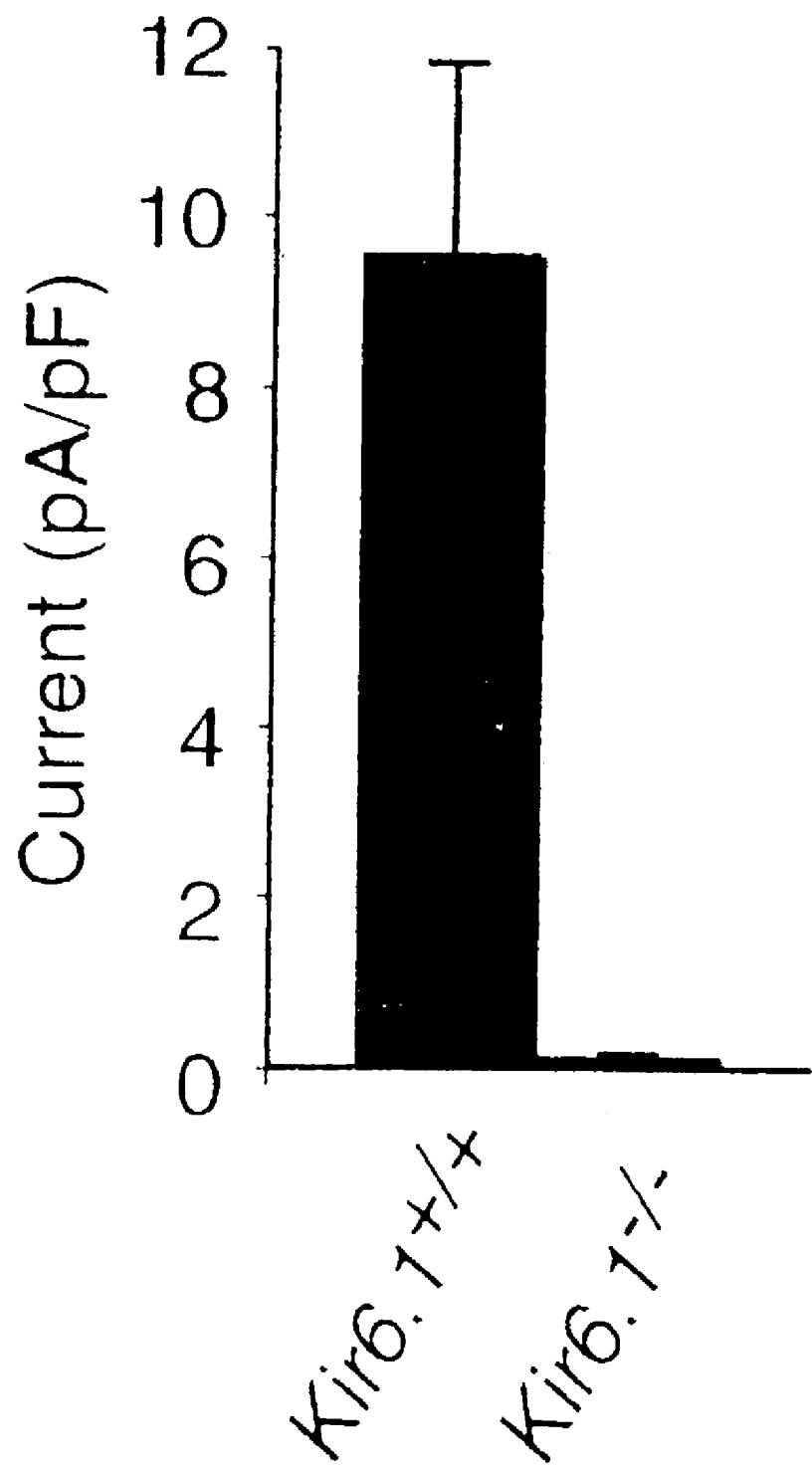

FIG. 15 is a graph showing the densities of glibenclamide-sensitive currents after 10 μM pinacidil application.

Figure 16:
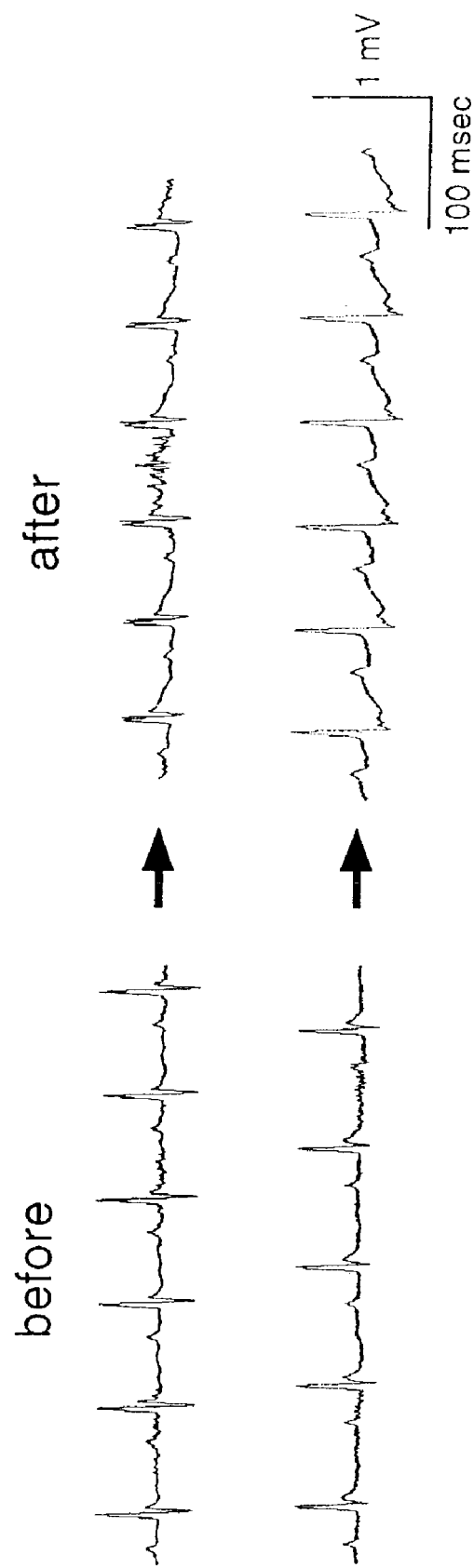

FIG. 16 shows ECGs before and after intravenous injection methylergometrine in Kir6.1$^{-/-}$ mice in vivo.

Figure 17:
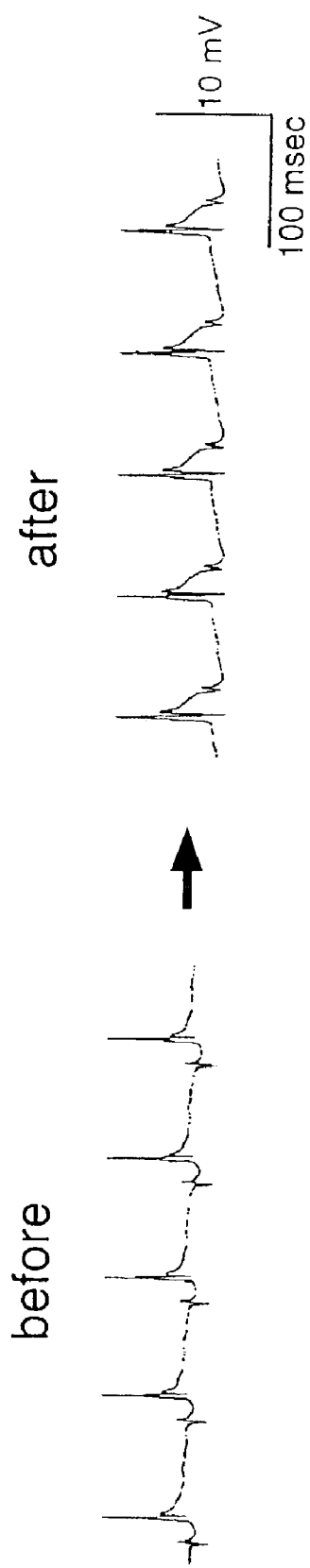

FIG. 17 shows ECGs before and after intravenous injection methylergometrine in Kir6.1$^{-/-}$ mice in vitro.

DETAILED DESCRIPTION OF THE INVENTION

The present invention will be described in further detail below with reference to examples. However, it is not intended that the present invention be limited to those examples.

EXAMPLES

[Generation of Kir6.1$^{-/-}$ Mice]

<Gene Targeting for Kir6.1$^{-/-}$ Mice>

Figure 1:
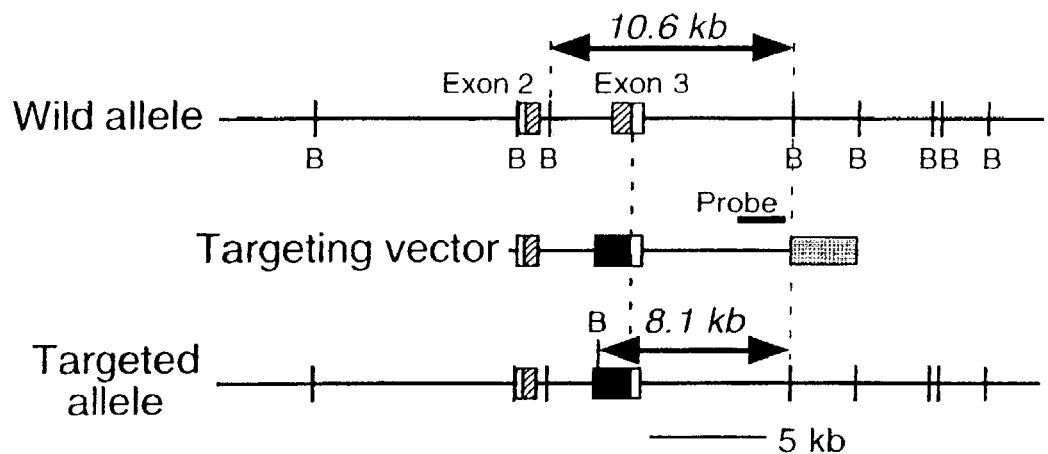
FIG. 1 illustrates maps of the Kir6.1 locus, targeting vector and the resulting targeted locus, which has been site-specifically disrupted. The open, shaded, filled and gray boxes indicate untranslated exon, protein-coding exon, neomycin resistant gene and thymidine kinase gene, respectively. "B" denotes BamHI site.

The preset inventors generated mice lacking Kir6.1 by replacing a part of intron 2 and exon 3 of the Kir6.1 gene that includes the pore-forming region of the channel (FIG. 1). Briefly, the 129Sv mouse genomic library (in λDASH phage library) was screened using a full length of the coding region of mouse Kir6.1 cDNA (SEQ ID NO:2) (nt. 1-1275). Twelve positive clones were isolated and the restriction enzyme map was constructed. Based on the restriction enzyme map thus obtained, a targeting vector was constructed by replacing, with the neomycin resistant-gene cassette, a fragment ranging from XbaI site in intron 2 located about 1.2 kb upstream of exon 3 to MroI site in exon 3 of the mouse Kir6.1 gene. Genomic 3.8 kb and 7.0 kb fragments were used as 5'- and 3'-arms, respectively. For negative selection, a thymidine kinase cassette was added in the 3' end of the targeting vector. The targeting vector was introduced into an ES cell line (R1) by electroporation and 130 surviving clones were picked up on the 8th day after the transfection. Clones having undergone homologous recombination were identified by Southern blotting. As a probe, a genomic 2.4 kb fragment (SphI-XhoI fragment) upstream of the 5'-arm of the targeting vector was used, and the genomic DNA was digested with SphI. Fourteen ES cell clones were shown to have undergone homologous recombination. Using these clones, chimeric mice were generated by aggregation and 4 independent mouse lines were obtained. Disruption of Kir6.1 gene was confirmed by genomic Southern blotting and Northern blotting. Those mice were backcrossed to a mouse strain C57BL6.

Figure 2:
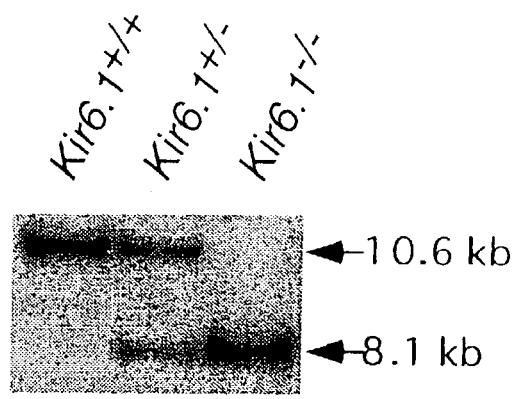
FIG. 2 shows Southern blot analysis of genomic DNA digested with BamHI from wild-type (Kir6.1$^{+/+}$), heterozygous (Kir6.1$^{+/-}$), and homozygous (Kir6.1$^{-/-}$) mutants. The probe indicated in FIG. 1 was used.
Figure 3:
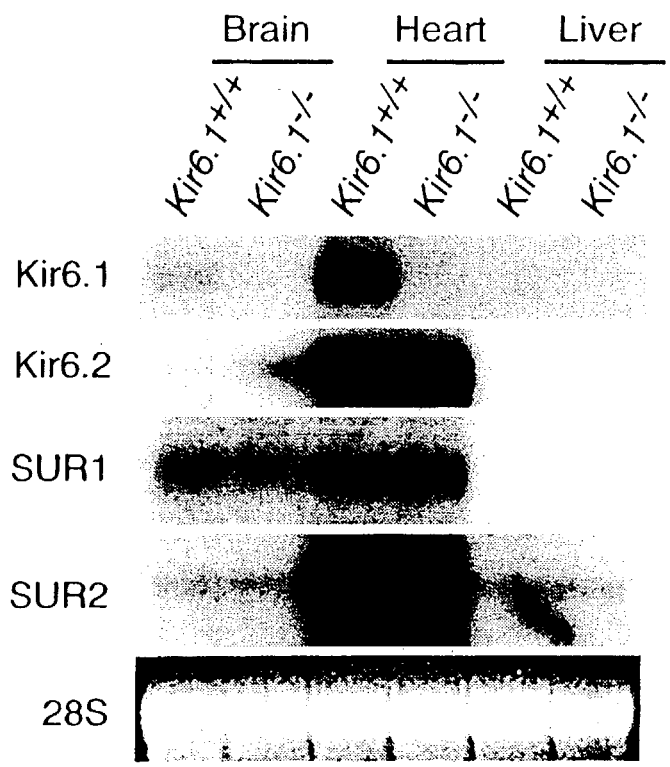
FIG. 3 shows Northern blot analysis of RNAs from Kir6.1$^{+/+}$ and Kir6.1$^{-/-}$ mice.

Homozygous knockout mice (Kir6.1$^{-/-}$) were generated by cross-breeding of the heterozygous. (Kir6.1$^{+/-}$) mice. Homologous recombination was confirmed by Southern blot analysis of genomic DNA isolated from the tail as described below (FIG. 2). Also confirmed was the lack of Kir6.1 mRNA expression. Changes in the mRNA expression levels of various K$_{ATP}$ channel subunits (Kir6.2, SUR1 and SUR2) were examined by Northern blotting as described below (FIG. 3). The mRNA expression levels of Kir6.2, SUR1 and SUR2 were similar in wild-type (Kir6.1$^{+/+}$) and Kir6.1$^{-/-}$ mice. This indicates that their regulation is independent of Kir6.1 and that the other subunits are unable to compensate for the loss of Kir6.1 at the transcription level.

<Methods of Southern- and Northern-Blot Analysis>

Genomic DNA (for Southern blotting) and total RNA (for Northern blotting) were prepared from mice tails and tissues following standard procedures. DNA (10 μg) or RNA (20 μg) was subjected to electrophoresis on a 1% agarose gel and blotted onto a nylon membrane. Hybridization was performed under highly stringent conditions with $^{32}$P-labeled probes. The probe used for the Southern blotting was a genomic fragment of Kir6.1 as shown in FIG. 1 (from SphI site to BamI site) (SEQ ID NO:3). The probes used for the Northern blotting were as follows.

(1) a cDNA fragment of mouse Kir6.1 [the fragment corresponding to the nucleotides 1–1330 of the nucleotide sequence of GenBank Accession No. D88159 (SEQ ID NO:4) (including nucleotides 1–203 in the 5'-untranslated region and nucleotides 1479–1712 in the 3'-untranslated region).

(2) a cDNA fragment of mouse Kir6.2 [the fragment corresponding to the nucleotides +134–+1064 of the nucleotide sequence of GenBank Accession No. NM_010602 (SEQ ID NO:5)]

(3) a cDNA fragment of human SUR1 [the fragment corresponding to the nucleotides 185–1250 of the nucleotide sequence of GenBank Accession No. AF087138 (SEQ ID NO:6)]

(3) cDNA fragment of rat SUR2 [rat SUR2A, the fragment corresponding to the nucleotides 39–1118 of the nucleotide sequence of GenBank Accession No. NM_013040 (SEQ ID NO:7)]

[Rearing and Observation of Kir6.1$^{-/-}$ Mice]

Figure 4:
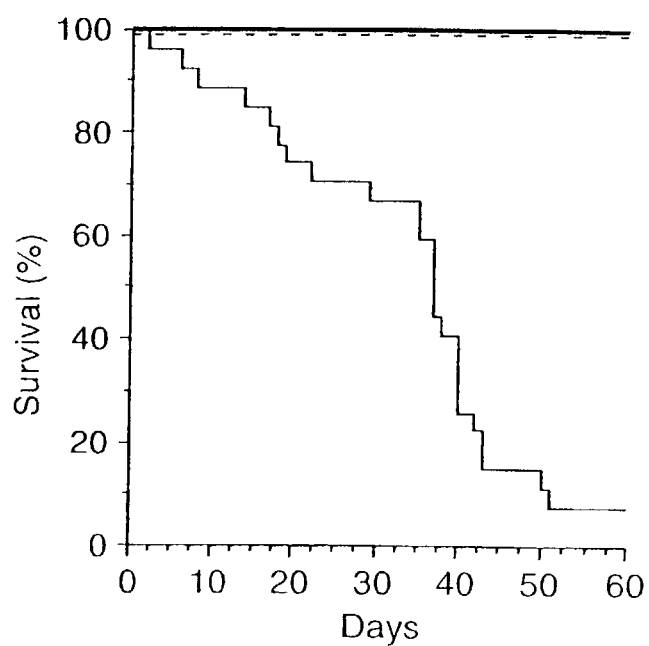
FIG. 4 is a graph illustrating the survival rates (%) after birth of Kir6.1$^{+/+}$ (thick line, n=36), Kir6.1$^{+/-}$ (dotted line, n=67), and Kir6.1$^{-/-}$ n=27) mice.

Analysis of 136 offspring mice showed that the number of Kir6.1$^{-/-}$ mice was only slightly less than what was expected according to Mendel's laws (approximately 5%). However, Kir6.1$^{-/-}$ mice were prone to premature death, the majority dying between 5 and 6 weeks after birth (FIG. 4). Those animals were found dead, so-called sudden death, within 24 hours after they were observed to be normal in behavior and activity levels.

[Drugs]

The following drugs were used in the experiments described below: pinacidil (SIGMA), glibenclamide (SIGMA CHEMICAL). Pinacidil was dissolved in physiological saline containing 0.1 N hydrochloric acid. Glibenclamide was dissolved in DMSO (final concentration of the solvent less than 0.1% in the tests).

[Statistical Analysis]

All the data in the experiments were presented as mean±SE. Statistical analysis of the data was performed using an analysis of variance (ANOVA) to the difference among wild-type and Kir6.1$^{-/-}$ mice, regarding p-values of <0.05 as being significant.

[Electrophysiological Examination of Mouse Heart by Electrocardiograph]

To determine if cardiac electrophysiological dysfunction contribute to sudden death of Kir6.1$^{-/-}$ mice, electrocardiograms (ECGs) from wild (Kir6.1$^{+/+}$) mice and Kir6.1$^{-/-}$ mice were monitored using implantable radio telemetry (FIGS. 5–8).

ECG recordings of conscious mice under unrestricted conditions were obtained using an implantable radio frequency transmitter (TA10ETA-F20) (DATA SCIENCES, St. Paul, Minn.), with subcutaneous leads placed in the conventional lead II position. ECGs of anesthetized mice and isolated hearts (Langendorff-perfused heart) were recorded with leads placed on the body surface (lead II) or epicardium.

Figure 5:
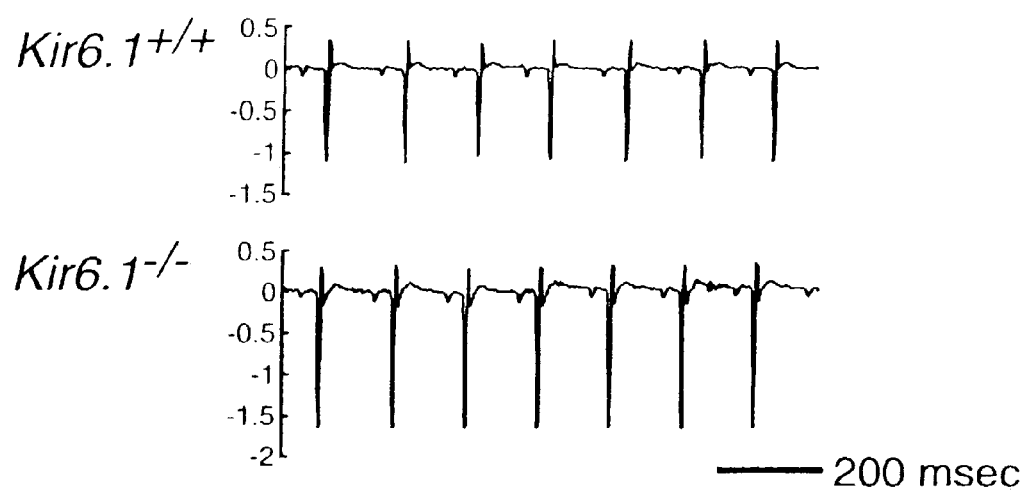
FIG. 5 shows Normal ECGs from Kir6.1$^{+/+}$ (upper) and Kir6.1$^{-/-}$ (lower).
Figure 6:
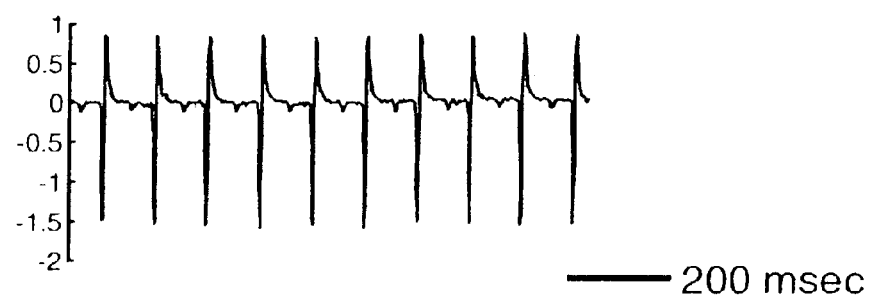
FIG. 6 shows spontaneous ST elevation in ECG recorded from a Kir6.1$^{-/-}$ mice.
Figure 7:
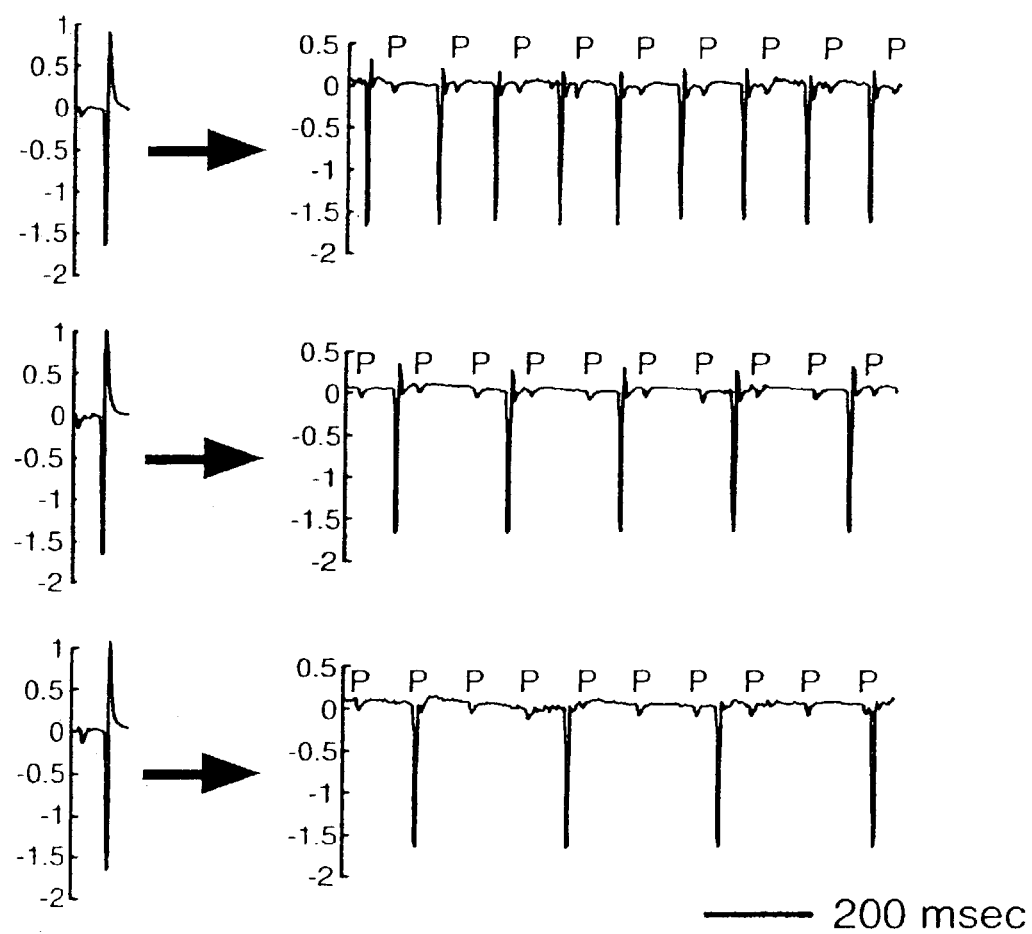
FIG. 7 shows the 1st (top), 2nd (middle) and 3rd (bottom) AV block, and ST elevation (left) preceding each occurrence. "P" indicates P wave.
Figure 8:
FIG. 8 is shows representative ECG of marked bradycardia in one of two Kir6.1$^{-/-}$ mice that died during ECG monitoring.

During most of the monitoring period, the heart rate (HR, bpm), QRS time (ms), and PR interval (ms) in Kir6.1$^{-/-}$ mice (n=4) were similar to those in Kir6.1$^{+/+}$ mice (n=4) (FIG. 5). However, all of the Kir6.1$^{-/-}$ mice (4/4) exhibited spontaneous elevation of ST segment lasting for several seconds to almost a minute (FIG. 6). After a latency period ranging from several seconds to a few minutes from onset of ST elevation, atrioventricular (AV) blocks of various degrees occurred in all cases (FIGS. 6–8). The 1st, 2nd or 3rd AV blocks were observed in all of the Kir6.1$^{-/-}$ mice (4/4), but no ST-T change or AV block appeared in the Kir6.1$^{+/+}$ mice (0/4). Two Kir6.1$^{-/-}$ mice out of the four died during the recording period, showing spontaneous ST elevation leading to a persistent 3rd AV block, during which the R-R intervals gradually lengthened until cessation of heart beat. Thus, the cause of death in Kir6.1$^{-/-}$ mice seems to be associated with myocardial ischemia.

[Electrophysiological Studies of Cardiomyocytes]

Kir6.1 is expressed most abundantly in the heart (24), and is present in cardiomyocytes (25). Therefore, electrophysiological properties of ventricular myocytes isolated from Kir6.1$^{+/+}$ and Kir6.1$^{-/-}$ mice were compared. The quasi-steady-state membrane currents were recorded using a ramp-pulse protocol.

Briefly, single ventricular cells of the heart were enzymatically isolated and whole-cell membrane currents were recorded by the patch-clamp method (13). The pipette solution was composed of 20 mM KCl, 1 mM MgCl$_2$, 1 mM phosphocreatine-K$_2$, 110 mM K$_1$-aspartate, 1 mM K$_2$-ATP, 1.0 mM EGTA, 5 mM HEPES (pCa 8.0, pH 7.4). The external solution used was a HEPES-Tyrode solution containing 143 mM NaCl, 5.4 mM KCl, 1.8 mM CaCl$_2$, 0.5 mM MgCl$_2$, 0.33 mM NaHPO$_4$, 0.55 mM glucose, 5 mM HEPES (pH 7.4). Voltage- and current-clamp experiments in heart cells were performed at 36.0° C.

Figure 9:
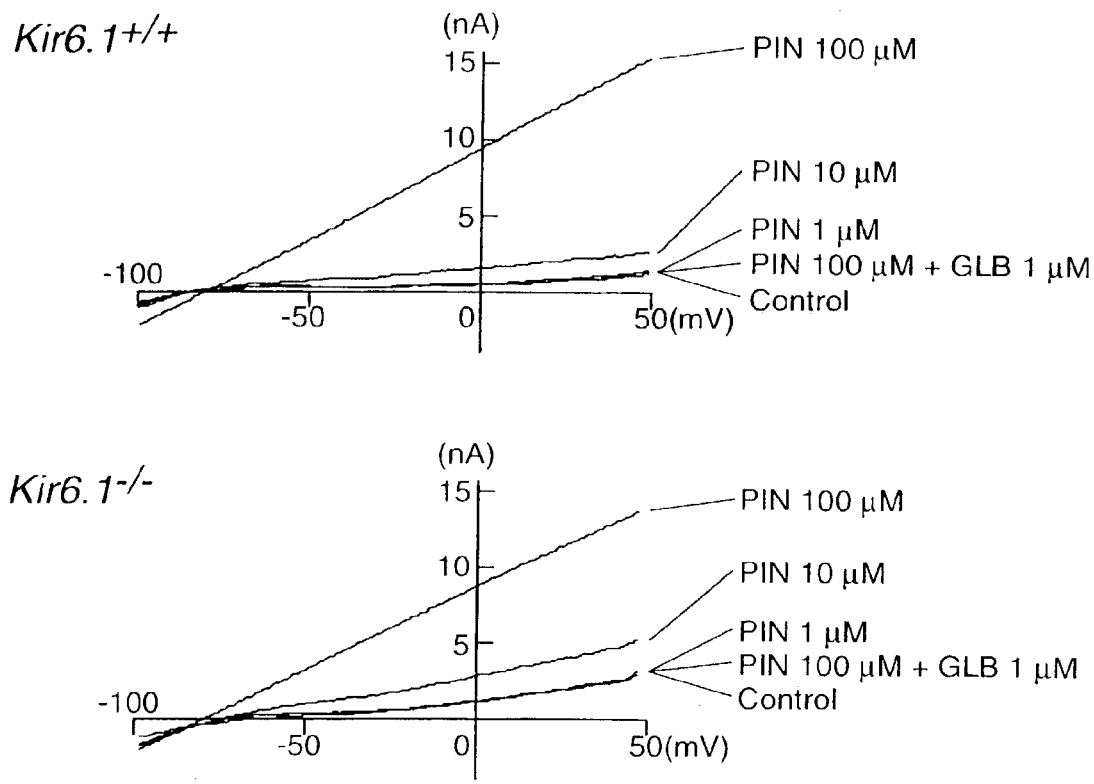
FIG. 9 shows an example of records of whole-cell membrane currents of Kir6.1$^{+/+}$ mice (upper) and Kir6.1$^{-/-}$ mice (lower), showing the effects of pinacidil and glibenclamide on whole-cell membrane currents. PIN=pinacidil, GLB=glibenclamide
Figure 10:
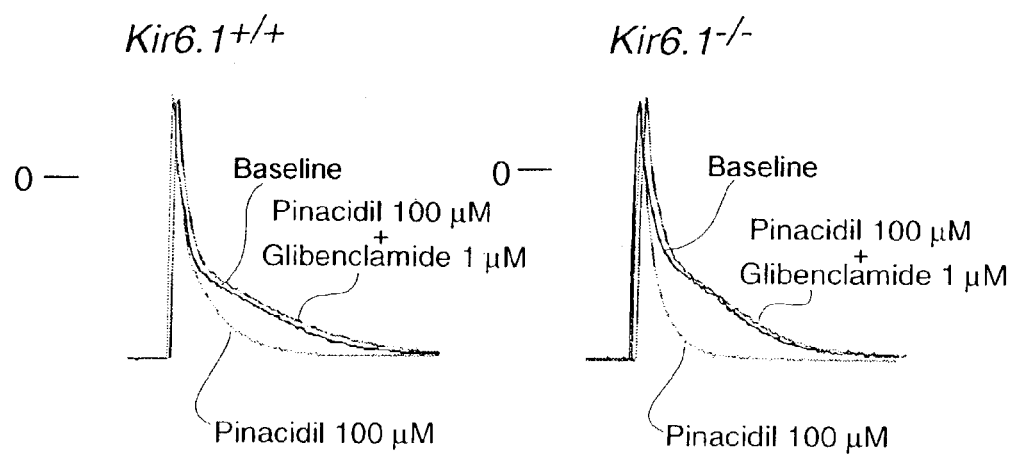
FIG. 10 shows measured effects of pinacidil and glibenclamide on action potentials in Kir6.1$^{+/+}$ mice (left) and Kir6.1$^{-/-}$ mice (right).

Results:

The reversal potential was close to the potassium equilibrium potential in ventricular cells of both Kir6.1$^{+/+}$ (6 cells from 3 animals) and Kir6.1$^{-/-}$ (5 cells from 3 animals) mice (FIG. 9). In both groups of cells, a K channel opener pinacidil produced concentration-dependent increases of an outward current, which was blocked by 1 μM glibenclamide, indicating and ATP-sensitive K$^+$ current (I$_{K,ATP}$). There were no significant differences in the density of the outward current between Kir6.1$^{+/+}$ and Kir6.1$^{-/-}$ mice at 0 mV, either under control condition or after 1, 10 or 100 μM pinacidil, and 100 μM pinacidil plus 1 μM glibenclamide. There were no significant differences in baseline action potential parameters between Kir6.1$^{+/+}$ and Kir6.1$^{-/-}$ ventricular cells. Pinacidil shortened the action potential duration (APD) in both Kir6.1$^{+/+}$ (14 cells from 4 animals) and Kir6.1$^{-/-}$ (9 cells from 4 animals) ventricular cells (FIG. 10). APD at 90% repolarization level (APD$_{90}$) of Kir6.1$^{+/+}$ and Kir6.1$^{-/-}$ cells were shortened significantly from 31.6±2.3 ms to 18.3±2.2 ms and from 31.1±4.2 ms to 18.3±3.9 ms, respectively, by 100 μM pinacidil, which reversed to control levels after addition of 1 μM glibenclamide.

[Measurement of Aortic Blood Pressure]

K$^+$ channel openers are known to lower arterial blood pressure by relaxing vascular smooth muscles by opening vascular K$_{ATP}$ channels. The present inventors examined the vasodilation response to the K⁺ channel opener pinacidil in Kir6.1$^{+/+}$ and Kir6.1$^{-/-}$ mice, in vivo at first.

Hemodynamic measurements were carried out according to the method described by, Suzuki, et al. (12). Changes of mean arterial pressure (MAP) after intravenous injection of 0.3 mg/kg pinacidil are indicated on the ordinate. The points show mean±SE of 6 animals for both groups.

Figure 11:
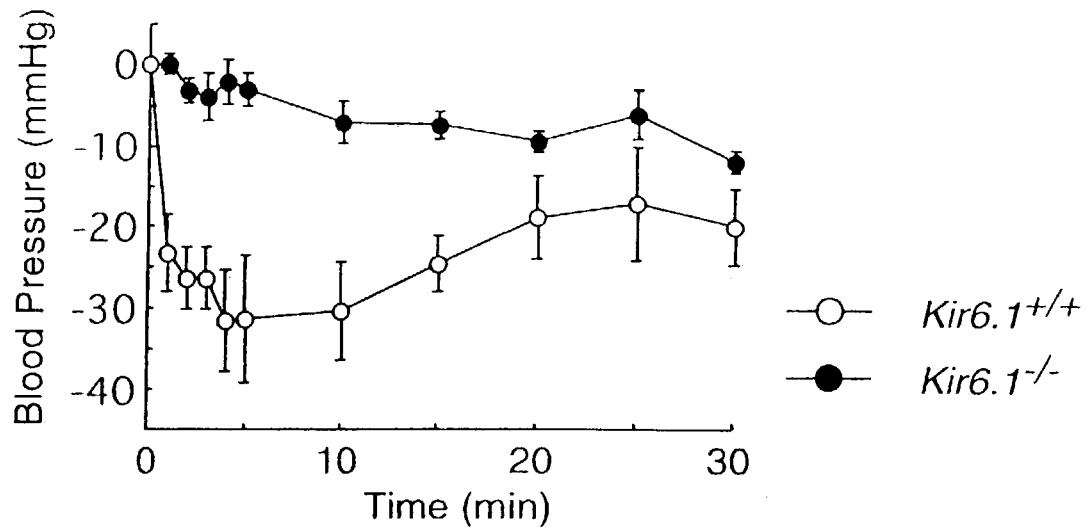
FIG. 11 is a graph showing the effects of pinacidil on mean arterial pressure (MAP) in anesthetized mice. The changes in pressure are expressed as the deference from the basal value.

Results:

Basal hemodynamic values of the mice, including heart rate (HR) and mean arterial pressure (MAP), were comparable between Kir6.1$^{+/+}$ and Kir6.1$^{-/-}$ mice under anesthesia with urethane [HR: 602±28 beats/min for Kir6.1$^{+/+}$ mice and 659±17 beats/min for Kir6.1$^{-/-}$ mice, MAP: 65±9 mmHg for Kir6.1$^{+/+}$ mice and 67±7 mmHg for Kir6.1$^{-/-}$ mice]. Intravenous injection of pinacidil (0.3 mg/kg) caused decrease in MAP by about 30 mmHg within 5 minutes in Kir6.1$^{+/+}$ mice but not in Kir6.1$^{-/-}$ mice (FIG. 11).

[Measurement of Aortic Contraction in Isolated Aortic Preparation]

Figure 12:
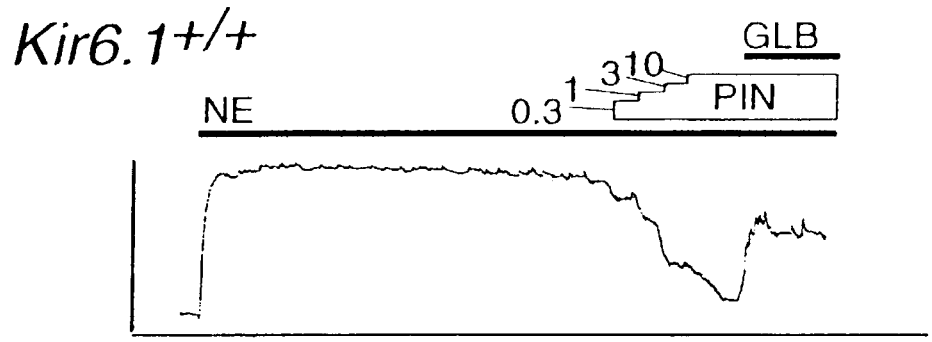
FIG. 12 shows the effects of pinacidil (PIN) and glibenclamide (GBL) on vasodilation in aortic rings from Kir6.1$^{+/+}$ mice (upper) and Kir6.1$^{-/-}$ mice (lower).
Figure 12:
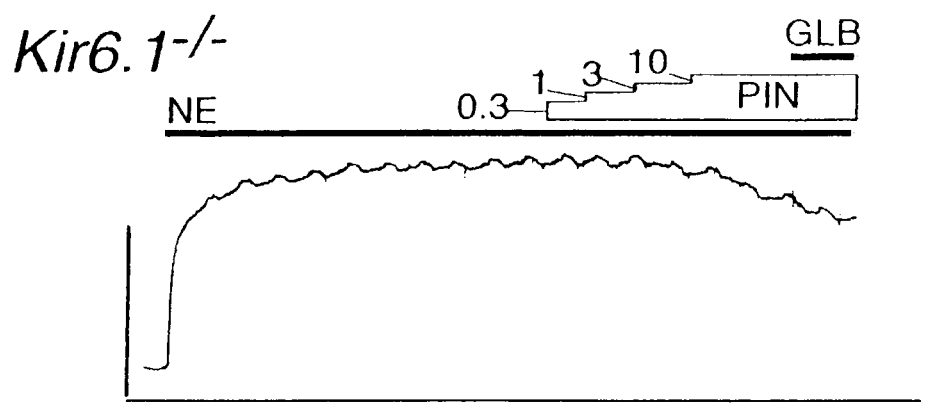

The vasodilation response of thoracic aorta to the K⁺ channel opener was further examined in vitro by measuring changes in the tension of aortic rings isolated from Kir6.1$^{+/+}$ and Kir6.1$^{-/-}$ mice (FIG. 12).

In the same manner as described by Suzuki et al. (13), mechanical function studies of isolated thoracic aorta were carried out. Briefly, the thoracic aorta without the endothelium was removed and cut into rings (4 mm in length). For isometric tension recording, the rings were mounted in a thermostatic organ bath. The bath was perfused with Krebs-Henseleit solution gassed with 95% $O_2$/5% $CO_2$. The aortic rings were precontracted by 0.1 μM norepinephrine, and pinacidil was added in a cumulative manner.

Results:

In Kir6.1$^{+/+}$ mice (5 samples from 4 animals), pinacidil produced a concentration-dependent vasodilating effect (FIG. 12, upper panel). In contrast, pinacidil din not elicit any $K_{ATP}$ channel-mediated vasodilating effect on rings isolated from Kir6.1$^{-/-}$ mice (5 samples from 4 animals) (FIG. 12, lower panel).

[Electrophysiological Studies of Smooth Muscle Cells of the Aorta]

As Kir6.1$^{-/-}$ mice were found to lack a vasodilation response of aorta to K⁺ channel openers both in vivo and in vitro, a study was carried out to examine if glibenclamide sensitive $K_{DNP}$ channel currents (19) could be detected in the aortic vascular smooth muscles of Kir6.1$^{+/+}$ mice.

Single smooth muscle cells of thoracic aorta were enzymatically isolated and electrophysiological studies were conducted in the same manner as performed in the cardiomyocytes.

The compositions of the extracellular high K⁺ solution and the pipette solution used in this smooth muscle cell experiment were as follows. The external high-K⁺ solution: 2.9 mM NaCl, 140 mM KCl, 2.2 mM $CaCl_2$, 1.2 mM $MgCl_2$, 14 mM glucose and 10 mM HEPES-KOH buffer (pH 7.4). The pipette solution: 140 mM KCl, 4 mM $MgCl_2$, 1 mM ATP-$K_2$, 10 mM EGTA and 10 mM HEPES-KOH solution (pH 7.2). The membrane current was measured at room temperature.

Effect of 10 mM pinacidil was tested on whole-cell membrane currents of aorta smooth muscle cells held at −40 mV in high K⁺ (140 mM) solution.

Results:

Pinacidil elicited significant inward K⁺ currents that were blocked by glibenclamide in Kir6.1$^{+/+}$ smooth muscle cells of, but failed to evoke any appreciable K⁺ currents in Kir6.1$^{-/-}$ cells (9.53±2.32 pA/pF for Kir6.1$^{+/+}$, 0.13±0.07 pA/pF for Kir6.1$^{-/-}$, p<0.05) (FIG. 14). This clearly indicates the absence of the $K_{NDP}$ channel currents in the vascular smooth muscle isolated from the aorta of Kir6.1$^{-/-}$ mice.

[Induction of Spasm in Coronary Arteries by Methylergometrine in vivo and in vitro]

To link dysregulation of vascular tonus and sudden death in Kir6.1$^{-/-}$ mice, an examination was tried to induce vasospasm using methylergometrine, an ergot alkaloid that stimulates serotonergic receptors and directly triggers the vasoconstriction of vascular smooth muscles (26). Interestingly, intravenous injection of the ergometrine derivative methylergometrine (20 mg) in anesthetized Kir6.1$^{-/-}$ mice elicited prompt elevation (4 animals out of 8) (FIG. 16) and depression (1 animal out of 8) of ST segments on ECG, the former resembling that recorded by implantable radio telemetry in Kir6.1$^{-/-}$ mice (FIG. 6). Methylergometrine induced cardiac death concomitantly with changes in ECG (5 Kir6.1$^{-/-}$ mice out of 8), although none of 7 Kir6.1$^{+/+}$ mice exhibited significant changes in ECG nor died after injection of the drug. Administration of methylergometrine also provoked similar changes in ECG in vitro in Langendorff-perfused hearts of Kir6.1$^{-/-}$ mice, and methylergometrine (20 mg) induced elevation of the ST segment in isolated hearts of Kir6.1$^{-/-}$ mice (4/4) but not in those of Kir6.1$^{+/+}$ mice (0/5) (FIGS. 16 and 17).

[Discussion]

As described above, Kir6.1$^{-/-}$ mice exhibited a high rate of sudden cardiac death (SCD) that is associated with spontaneous ST elevation on ECG followed by a series of AV blocks. Sudden cardiac death (SCD) is thought to be the principal cause of unexpected, rapid death in adults and infants (30). Although most SCD occurs in patient with some cardiac disease such as coronary atherosclerosis, myocardial disease, and inflammatory cardiac disease, some SCD occur unexpectedly due to abrupt cardiac arrest caused by arrhythmia or myocardial ischemia. Genetic abnormalities of ion channels [K⁺ (KVLQT1, HERG, KCNE1 or MiRP1), Na⁺ or $Ca^{2+}$ channel subunits] (31), a gap junction protein (connexin40) (32), and cardiac specific transcription factors (Nkx2.5 and HF-1b) (33) have so far been shown to be involved in SCD caused by lethal arrhythmia in human and mouse. Of these, abnormalities in K⁺, Na⁺, and $Ca^{2+}$ channels affect depolarization and repolarization of cardiomyocytes and cause long-QT syndrome in human and mouse. In cardiomyocytes isolated from mouse models of long-QT syndrome (34–36), abnormal ion currents were detected on the plasma membrane. In Kir6.1$^{-/-}$ mice, however, no electrophysiological abnormality was found in the plasma membrane of cardiomyocytes, despite the fact that Kir6.1 is expressed most abundantly in the heart (24). In addition, it was found that normal $K_{ATP}$ channels are present in cardiomyocytes of Kir6.1$^{-/-}$ mice. Accordingly, Kir6.2 but not Kir6.1 is a constituent of the $K_{ATP}$ channels of the plasma membrane of cardiomyocytes. The lack of abnormality in the electrophysiological properties of cardiomyocytes of Kir6.1$^{-/-}$ mice indicates that the pathophysiology of the AV block in Kir6.1$^{-/-}$ mice differs from that of long-QT syndrome due to K⁺, Na⁺ or $Ca^{2+}$ channel dysfunction. Alternatively, the AV block is due to the spontaneous ST elevation caused by myocardial ischemia. In contrast to the normal electrophysiological properties of Kir6.1$^{-/-}$ cardiomyocytes, it was found that the $K_{NDP}$ channels of the smooth muscle of the aortae were defective in Kir6.1$^{-/-}$ mice. The present inventors previously reported that $K_{NDP}$ channels in vascular smooth muscles are normal in Kir6.2 knockout mice (13). The present findings indicate that Kir6.1 is a constituent of the $K_{NDP}$ channel in plasma membrane of vascular smooth muscle cells. The lack of vasodilation response of Kir6.1$^{-/-}$ mice to pinacidil, both in vivo (blood pressure decrease) and in vitro (relaxation of aortic rings), indicates that the Kir6.1-containing $K_{NDP}$ channels play a critical role in the relaxation of vascular tonus.

The most remarkable finding in Kir6.1$^{-/-}$ mice is spontaneous coronary spasm leading to lethal AV block, a phenotype resembling Prinzmetal angina (or variant angina) in human. Prinzmetal angina is an unusual form of unstable angina reported by Prinzmetal et al. in 1959, which occurs almost exclusively at rest and is associated with elevation of ST segments on ECG during the attack (22). The pathophysiology of Prinzmetal angina is thought to be hyper contractility of epicardial coronary arteries, with or without atherosclerotic changes (23, 37). Although in most cases of Prinzmetal angina, the attack disappears spontaneously, it can lead to myocardial infarction, sever AV block, life threatening ventricular tachycardia, and sudden death if the coronary vasospasm is prolonged (38). Prinzmetal angina is diagnosed by detection of elevated ST segments on ECG during the attack or by induction of coronary spasm using ergot alkaloids or acetylcholine (23). Because sudden death of Kir6.1$^{-/-}$ mice is associated with spontaneous ST elevation (AV block), and administration of the ergot alkaloid methylergometrine elicited changes in ST segments (elevation or depression) in Kir6.1$^{-/-}$ mice both in vivo and in vitro, Kir6.1$^{-/-}$ mice represent an animal model of Prinzmetal angina.

The Kir6.1$^{-/-}$ mice of the present invention provide a means for elucidation of the mechanism of onset of coronary arteries spasm, as well as for screening of agents for disorders of coronary arteries such as Prinzmetal angina.

REFERENCES

1. Jan, L. Y. et al., Voltage-gated and inwardly rectifying potassium channels., J. Physiol., 505:267–282(1997).
2. Nichols, C. G. et al., Inward rectifier potassium channels, Annu. Rev. Physiol, 59:171–191(1997).
3. Abraham, M. R. et al., Channelopathies of inwardly rectifying potassium channels, FASEB, J., 13:1901–1910 (1999).
4. Ashcroft, F. M. et al., Correlating structure and function in ATP-sensitive K$^+$ channels, Trends. Neurosci., 21:288–294(1998).
5. Aguilar-Bryan, L. et al., Molecular biology of adenosine triphosphate-sensitive potassium channels, Endocr. Rev., 20:101–135(1999).
6. Seino, S., ATP-sensitive potassium channels: a model of heteromultimeric potassium channel/receptor assemblies, Annu. Rev. Physiol., 61:337–362(1999).
7. Inagaki, N. et al., A family of sulfonylurea receptors determines the pharmacological properties of ATP-sensitive K$^+$ channels, Neuron, 16:1011–1017(1996).
8. Isomoto, S. et al., A novel sulfonylurea receptor forms with BIR (Kir6.2) a smooth muscle type ATP-sensitive K$^+$ channel, J. Biol. Chem., 271:24321–24324(1996).
9. Inagaki, N. et al., IK$_{ATP}$: an inward rectifier subunit plus the sulfonylurea receptor, Science 270, 1166–1170(1995).
10. Miki, T. et al., ATP-sensitive K$^+$ channels in the hypothalamus are essential for the maintenance of glucose homeostasis, Nat. Neurosci., 4:507–512(2001).
11: Miki, T. et al., Defective insulin secretion and enhanced insulin action in K$_{ATP}$ channel-deficient mice, Proc. Natl. Acad. Sci. USA, 95:10402–10406(1998).
12. Seghers, V., et al., Surn knockout mice. A model for K$_{ATP}$ channel-independent regulation of insulin secretion., J. Biol. Chem., 275:9270–9277(2000).
13. Suzuki, M., et al., Functional roles of cardiac and vascular ATP-sensitive potassium channels clarified by Kir6.2-knockout mice, Circ. Res. 88:570–577(2001).
14. Gross, G. J. et al., Sarcolemmal versus mitochondrial ATP-sensitive K$^+$ channels and myocardial preconditioning, Circ. Res., 84:973–979(1999).
15. Chutkow, W. A., et al., Disruption of Sur2-containing K$_{ATP}$ channels enhances insulin-stimulated glucose uptake in skeletal muscle, Proc. Natl. Acad. Sci. USA, 98:11760–11764(2001).
16. Ammala, C. et al., The sulphonylurea receptor confers diazoxide sensitivity on the inwardly rectifying K$^+$ channel Kir6.1 expressed in human embryonic kidney cells, J. Physiol. 494:709–714(1996).
17. Liu, Y. et al., Pharmacological comparison of native mitochondrial K$_{ATP}$ channels with molecularly defined surface K$_{ATP}$ channels, Mol. Pharmacol., 59:225–230 (2001).
18. Kono, Y. et al., The properties of the Kir6.1–6.2 tandem channel co-expressed with SUR2A, Pflugers. Arch., 440: 692–698(2000).
19. Yamada, M. et al., Sulphonylurea receptor 2B and Kir6.1 form a sulphonylurea-sensitive but ATP-insensitive K$^+$ channel, J. Physiol., 499:715–720(1997).
20. Dorschner, H. et al., Stoichiometry of sulfonylurea-induced ATP-sensitive potassium channel closure, Mol. Pharmacol., 55:1060–1066(1999).
21. Hambrock, A. et al., Characterization of a mutant sulfonylurea receptor SUR2B with high affinity for sulphonylureas and openers: differences in the coupling to Kir6.x subtypes. Mol. Pharmacol., 60:190–199(2001).
22. Prinzmetal, M. et al, Angina pectoris. 1. A variant form of angina pectoris: Preliminary report, Am. J. Med. 27:375–378(1959).
23. Maseri, A., Role of coronary artery spasm in symptomatic and silent myocardial ischemia, J. Am. Coll. Cardiol., 9:249–262(1987).
24. Erginel-Unaltuna, N., Genomic organization and expression of KCNJ8/Kir6.1, a gene encoding a subunit of an ATP-sensitive potassium channel, Gene, 211:71–78(1998).
25. Schnitzler, M. M. et al., ATP-sensitive potassium channels in capillaries isolated from guinea-pig heart, J. Physiol., 525:307–317(2000).
26. Egashira, K. et al., Mechanism of ergonovine-induced hyperconstriction of the large epicardial coronary artery in conscious dogs a month after arterial injury, Circ. Res., 71:435–442(1992).
27. Inagaki, N. et al., Cloning and functional characterization of a novel ATP-sensitive potassium channel ubiquitously expressed in rat tissues, including pancreatic islets, pituitary, skeletal muscle, and heart, J. Biol. Chem., 370:5691–5694(1995).
28. Beech, D. J. et al., K channel activation by nucleotide diphosphates and its inhibition by glibenclamide in vascular smooth muscle cells, Br. J. Pharmacol., 110:573–582(1993).

29. Standen, N. B. et al., Hyperpolarizing vasodilators activate ATP-sensitive K+ channels in arterial smooth muscle, Science, 245:177–180(1989).
30. Myerburg, R. J. et al., A frequency of sudden cardiac death and profiles of risk, Am. J. Cardiol., 80:10F-19F (1997).
31. Keating, M. T. et al., Molecular and cellular mechanisms of cardiac arrhythmias, Cell, 104:569–580(2001).
32. Gutstein, D. E. et al., Conduction slowing and sudden arrhythmic death in mice with cardiac-restricted inactivation of connexin43, Circ. Res., 88:333–339(2001).
33. Robbins, J. et al., Listening for hoof beasts in heart beats, Nat. Med., 6:968–970(2000).
34. Kupershmidt, S. et al, Replacement by homologous recombination of the minK gene with lacZ reveals restriction of minK expression to the mouse cardiac conduction system, Circ. Res., 84:146–152(1999).
35. Drici, M. D. et al., Involvement of IsK-associated K+ channel in heart rate control of repolarization in a murine engineered model of Jervell and Lange-Nielsen syndrome, Circ. Res., 83:95–102(1998).
36. Barry, D. M. et al., Functional knockout of the transient outward current, Long-QT syndrome, and cardiac remodeling in mice expressing a dominant-negative Kv4 alpha subunit, Circ. Res., 83:560–567(1998).
37. Okumura, K. et al., Diffuse disorder of coronary artery vasomotility in patients with coronary spastic angina. Hyperreactivity to the constrictor effects of acetylcholine and the dilator effects of nitroglycerin, J. Am. Coll. Cardiol., 27:45–52(1996).
38. MacAlpin, R. N., Cardiac arrest and sudden unexpected death in variant angina: complications of coronary spasm that can occur in the absence of severe organic coronary stenosis, Am. Heart J., 125:1011–1017(1993).

The present disclosure relates to subject matter contained in priority Japanese Patent Application No.2002–076170, filed on Mar. 19, 2002, the contents of which is herein expressly incorporated by reference in its entirety.

What is claimed is:

1. A transgenic mouse comprising a homozygous disruption in the endogenous Kir6.1 gene, wherein said transgenic mouse exhibits sudden cardiac death, atrioventricular blockage, spontaneous cardiac ischemia, or spontaneous cardiac spasms.

* * * * *

SEQUENCE LISTING

```
<160> NUMBER OF SEQ ID NOS: 7

<210> SEQ ID NO 1
<211> LENGTH: 424
<212> TYPE: PRT
<213> ORGANISM: Mus musculus
<220> FEATURE:
<223> OTHER INFORMATION: Kir6.1

<400> SEQUENCE: 1

Met Leu Ala Arg Lys Ser Ile Ile Pro Glu Glu Tyr Val Leu Ala Arg
 1               5                  10                  15

Ile Ala Ala Glu Asn Leu Arg Lys Pro Arg Ile Arg Asp Arg Leu Pro
            20                  25                  30

Lys Ala Arg Phe Ile Ala Lys Ser Gly Ala Cys Asn Leu Ala His Lys
        35                  40                  45

Asn Ile Arg Glu Gln Gly Arg Phe Leu Gln Asp Ile Phe Thr Thr Leu
    50                  55                  60

Val Asp Leu Lys Trp Arg His Thr Leu Val Ile Phe Thr Met Ser Phe
65                  70                  75                  80

Leu Cys Ser Trp Leu Leu Phe Ala Ile Met Trp Trp Leu Val Ala Phe
                85                  90                  95

Ala His Gly Asp Ile Tyr Ala Tyr Met Glu Lys Gly Thr Met Glu Lys
            100                 105                 110

Ser Gly Leu Glu Ser Ala Val Cys Val Thr Asn Val Arg Ser Phe Thr
        115                 120                 125

Ser Ala Phe Leu Phe Ser Ile Glu Val Gln Val Thr Ile Gly Phe Gly
    130                 135                 140

Gly Arg Met Met Thr Glu Glu Cys Pro Leu Ala Ile Thr Val Leu Ile
145                 150                 155                 160

Leu Gln Asn Ile Val Gly Leu Ile Ile Asn Ala Val Met Leu Gly Cys
                165                 170                 175

Ile Phe Met Lys Thr Ala Gln Ala His Arg Arg Ala Glu Thr Leu Ile
            180                 185                 190

Phe Ser Arg His Ala Val Ile Ala Val Arg Asn Gly Lys Leu Cys Phe
        195                 200                 205
```

-continued

```
Met Phe Arg Val Gly Asp Leu Arg Lys Ser Met Ile Ile Ser Ala Ser
    210                 215                 220

Val Arg Ile Gln Val Val Lys Lys Thr Thr Thr Pro Glu Gly Glu Val
225                 230                 235                 240

Val Pro Ile His Gln Gln Asp Ile Pro Val Asp Asn Pro Ile Glu Ser
                245                 250                 255

Asn Asn Ile Phe Leu Val Ala Pro Leu Ile Ile Cys His Val Ile Asp
            260                 265                 270

Lys Arg Ser Pro Leu Tyr Asp Ile Ser Ala Thr Asp Leu Ala Asn Gln
        275                 280                 285

Asp Leu Glu Val Ile Val Ile Leu Glu Gly Val Val Glu Thr Thr Gly
    290                 295                 300

Ile Thr Thr Gln Ala Arg Thr Ser Tyr Ile Ala Glu Glu Ile Gln Trp
305                 310                 315                 320

Gly His Arg Phe Val Ser Ile Val Thr Glu Glu Gly Val Tyr Ser
                325                 330                 335

Val Asp Tyr Ser Lys Phe Gly Asn Thr Val Arg Val Ala Ala Pro Arg
                340                 345                 350

Cys Ser Ala Arg Glu Leu Asp Lys Pro Ser Ile Leu Ile Gln Thr
            355                 360                 365

Leu Gln Lys Ser Glu Leu Ser His Gln Asn Ser Leu Arg Lys Arg Asn
370                 375                 380

Ser Met Arg Arg Asn Asn Ser Met Arg Arg Asn Asn Ser Ile Arg Arg
385                 390                 395                 400

Asn Asn Ser Ser Leu Met Val Pro Lys Val Gln Phe Met Thr Pro Glu
                405                 410                 415

Gly Asn Gln Cys Pro Ser Glu Ser
            420
```

<210> SEQ ID NO 2
<211> LENGTH: 1275
<212> TYPE: DNA
<213> ORGANISM: Mus musculus
<220> FEATURE:
<223> OTHER INFORMATION: coding region of Kir6.1 cDNA

<400> SEQUENCE: 2

```
atg ttg gcc agg aag agc atc atc ccg gag gag tat gtg ctg gcg cgc      48
Met Leu Ala Arg Lys Ser Ile Ile Pro Glu Glu Tyr Val Leu Ala Arg
  1               5                  10                  15 atc gca gcg gag aac ctg cgc aaa ccg cgc atc cgc gac cgt ctc ccc      96
Ile Ala Ala Glu Asn Leu Arg Lys Pro Arg Ile Arg Asp Arg Leu Pro
             20                  25                  30 aaa gcc cgc ttc atc gcc aag agc gga gcc tgc aac ctg gca cac aag     144
Lys Ala Arg Phe Ile Ala Lys Ser Gly Ala Cys Asn Leu Ala His Lys
         35                  40                  45 aac atc cga gag caa ggt cgc ttc ctg cag gac atc ttc acc acc ttg     192
Asn Ile Arg Glu Gln Gly Arg Phe Leu Gln Asp Ile Phe Thr Thr Leu
     50                  55                  60 gta gac ctg aag tgg cgt cac acg ctg gtc atc ttc acc atg tcc ttc     240
Val Asp Leu Lys Trp Arg His Thr Leu Val Ile Phe Thr Met Ser Phe
65                  70                  75                  80 ctc tgc agc tgg ctg ctc ttc gct atc atg tgg tgg ctg gtg gct ttc     288
Leu Cys Ser Trp Leu Leu Phe Ala Ile Met Trp Trp Leu Val Ala Phe
                 85                  90                  95 gcc cac ggg gac atc tat gct tac atg gag aaa ggc acc atg gag aag     336
Ala His Gly Asp Ile Tyr Ala Tyr Met Glu Lys Gly Thr Met Glu Lys
            100                 105                 110
```

```
agt ggc ctg gag tcc gct gtc tgt gtg acc aat gtc agg tca ttc acg         384
Ser Gly Leu Glu Ser Ala Val Cys Val Thr Asn Val Arg Ser Phe Thr
        115                 120                 125 tct gcg ttt ctc ttc tcc att gag gtt caa gtg acc att ggg ttt gga         432
Ser Ala Phe Leu Phe Ser Ile Glu Val Gln Val Thr Ile Gly Phe Gly
    130                 135                 140 ggg aga atg atg act gag gaa tgc cct ctg gcc atc acg gtt ttg att         480
Gly Arg Met Met Thr Glu Glu Cys Pro Leu Ala Ile Thr Val Leu Ile
145                 150                 155                 160 ctg cag aac atc gtg ggt ctg atc atc aac gca gtc atg ttg ggc tgc         528
Leu Gln Asn Ile Val Gly Leu Ile Ile Asn Ala Val Met Leu Gly Cys
                165                 170                 175 atc ttc atg aag acg gcg cag gcc cac aga agg gca gag acg ctg att         576
Ile Phe Met Lys Thr Ala Gln Ala His Arg Arg Ala Glu Thr Leu Ile
            180                 185                 190 ttc agc cgc cat gct gtg att gcc gtc cgc aat ggc aag ctg tgc ttc         624
Phe Ser Arg His Ala Val Ile Ala Val Arg Asn Gly Lys Leu Cys Phe
        195                 200                 205 atg ttc cgg gtg ggt gac ctg agg aag agc atg atc att agc gcc tcg         672
Met Phe Arg Val Gly Asp Leu Arg Lys Ser Met Ile Ile Ser Ala Ser
    210                 215                 220 gtg cgc atc cag gtg gtc aag aaa acc acg acg cca gaa ggg gag gtg         720
Val Arg Ile Gln Val Val Lys Lys Thr Thr Thr Pro Glu Gly Glu Val
225                 230                 235                 240 gtg cct att cat cag cag gac att cct gtt gat aat ccc atc gag agc         768
Val Pro Ile His Gln Gln Asp Ile Pro Val Asp Asn Pro Ile Glu Ser
                245                 250                 255 aat aat atc ttc cta gtg gcc cca ttg atc atc tgc cac gtg att gac         816
Asn Asn Ile Phe Leu Val Ala Pro Leu Ile Ile Cys His Val Ile Asp
            260                 265                 270 aag cgt agc ccc ctg tat gat atc tca gca act gac ctt gcc aat caa         864
Lys Arg Ser Pro Leu Tyr Asp Ile Ser Ala Thr Asp Leu Ala Asn Gln
        275                 280                 285 gac ctg gag gtc ata gtg att ctc gag ggc gtg gta gaa acc aca ggc         912
Asp Leu Glu Val Ile Val Ile Leu Glu Gly Val Val Glu Thr Thr Gly
    290                 295                 300 atc acc aca caa gca cgg acc tcc tac att gcc gag gag atc cag tgg         960
Ile Thr Thr Gln Ala Arg Thr Ser Tyr Ile Ala Glu Glu Ile Gln Trp
305                 310                 315                 320 gga cac cgc ttc gtg tca att gtg act gag gag gag ggc gtg tac tct        1008
Gly His Arg Phe Val Ser Ile Val Thr Glu Glu Glu Gly Val Tyr Ser
                325                 330                 335 gtg gac tat tcc aaa ttt ggt aac acg gtg aga gtg gct gcg cca aga        1056
Val Asp Tyr Ser Lys Phe Gly Asn Thr Val Arg Val Ala Ala Pro Arg
            340                 345                 350 tgc agt gcc cgg gag ctg gat gag aag cct tcc atc ctg att cag acc        1104
Cys Ser Ala Arg Glu Leu Asp Glu Lys Pro Ser Ile Leu Ile Gln Thr
        355                 360                 365 ctc caa aag agc gaa ctg tcg cac cag aat tct ctg cgg aag cgc aac        1152
Leu Gln Lys Ser Glu Leu Ser His Gln Asn Ser Leu Arg Lys Arg Asn
    370                 375                 380 tcc atg agg aga aac aac tcc atg agg aga aac aac tcc atc agg agg        1200
Ser Met Arg Arg Asn Asn Ser Met Arg Arg Asn Asn Ser Ile Arg Arg
385                 390                 395                 400 aat aac tct tcc ctc atg gtg ccc aag gtg cag ttc atg act cca gaa        1248
Asn Asn Ser Ser Leu Met Val Pro Lys Val Gln Phe Met Thr Pro Glu
                405                 410                 415 gga aac cag tgt cca tca gaa tca tga                                    1275
Gly Asn Gln Cys Pro Ser Glu Ser
            420
```

<210> SEQ ID NO 3
<211> LENGTH: 2148
<212> TYPE: DNA
<213> ORGANISM: Mus musculus
<220> FEATURE:
<223> OTHER INFORMATION: Kir6.1 genomic DNA fragment

<400> SEQUENCE: 3

| | | | | | |
|---|---|---|---|---|---|
| gcatgcacat | atgtgtatgt | gcacgagagc | agtgcccaca | aagattagac | ctaggtatca | 60 |
| ggtcccctgg | aggtggggct | ctcagtggct | atgaactgcc | atgtgagtgt | tgaactctgg | 120 |
| gagagccaca | ggtgttctta | ccacaaagct | gcctctccag | ccccaagtaa | agttgttctg | 180 |
| gagccaagag | ttggaagtca | cgtatcggct | tctgttcaaa | gtcttttaat | ttaaaatcag | 240 |
| gcatatgtcc | attggaaaag | ctgaaagctg | tcgaatctat | aaccaaatgg | tcacatttct | 300 |
| agaaagggaa | aaactgtagc | tatgaactac | aggaaggggt | ctgagaggag | agagcatcta | 360 |
| ccagcttcat | ggcactaagt | atttaagcaa | atgctgtgat | aaatagtctg | aagacaaggg | 420 |
| cggggggagg | ggattgaaat | gatttatgat | ttcaatttat | gaatgaaatg | aatatgaaat | 480 |
| ggcaataagt | agggaggtgg | gaggtttgaa | agagcatatt | ggtaaaagga | gagaatttta | 540 |
| gcttaggtag | cttacagctc | tgtgtggtac | ctctctctgt | ctctctgcct | ctctctcttt | 600 |
| ctctctctgt | ctctttcttt | ctctctccat | ttcaatctcc | atctatctat | attatctcta | 660 |
| tatacatata | tgccataatc | tatatctata | tgataattta | tatctctgta | tatcactatc | 720 |
| atttatacta | catctccatc | tctgtcgata | tagatgatat | aaacagacag | atgcagtctt | 780 |
| tggtgaactt | gaggagatat | acagagttgg | gaatgaagct | ggaaaatgaa | cccaggaagc | 840 |
| cacatcagag | accaggtaga | aaagtcctgg | ctgtcattcc | cgaaaaggtt | ggtctttctc | 900 |
| cagttgccta | tgtccaatac | ttgaagcctt | tggcgaactc | tattgagttc | tattgaactc | 960 |
| tatttctaac | tgagaagggg | atcgtgacct | taattttgca | taccaccagt | tcatcttttg | 1020 |
| cattgtcaac | acaaactgaa | gcaagccagt | ggtatgtaga | tatttagcct | caatctgtgt | 1080 |
| tcatgcatac | atgtttgtgt | gtgaagatgg | tgcatatgtc | aggtgtgtat | tgttaaaaaa | 1140 |
| atatgcatgt | ggaggccaga | cattgatact | aggtaccttg | ttgtttgttg | ttttattttt | 1200 |
| tgagacagga | tctctcattg | actgacctgg | ggctcatcac | tgtggctagg | ctgactggtc | 1260 |
| agcaactcca | gggagtgcct | gtttgtattc | ccgatgctct | ggagttagag | atgcatgaag | 1320 |
| ctgtgacagg | tagggatgtg | gattctgggt | ccaaacttag | ttctgcccac | ttgcacagca | 1380 |
| agcacatcac | ccagtgagcc | tgtcttcact | gctgggtatt | cgttttttaca | tcactaaaat | 1440 |
| aaactgttct | tgatacaata | gtttcacctc | agttaccccca | gagagaatca | gagggacatc | 1500 |
| agaggcttcc | aatgtaggta | gcaaagtcct | tggtgggtgt | ggggagcca | cttgaaaaag | 1560 |
| aggattgatg | aagatgtaag | acctctaatc | agacttagcc | ccaatgcctt | atcttgacct | 1620 |
| gacattaaag | gccgattaag | attttcacga | acttgaactt | gaatctttgc | agtaaattac | 1680 |
| cagcgagcat | aattggagtc | acatcctctg | aaggtctgtg | gggaattccc | gtcacatttg | 1740 |
| atgagaatcg | tgtagaaaga | tcctgggaag | agcgtggccc | ttgagcttcc | tcttgagccc | 1800 |
| cctgtagggt | ttgttgtgga | tactttcaca | cactgctcct | tggagacaca | aatttcagtc | 1860 |
| ctttctctgt | cttctacatc | ctgacagtaa | tgcaatgaag | gagaagcaga | agtcttctcg | 1920 |
| ttcttcttta | tctgagatga | atttactcat | caaagaggaa | aattctttca | ctataaattg | 1980 |
| caaatcacaa | cacaacatca | acaagaggag | gaaatgcttc | actacgctta | ctgatgacaa | 2040 |

```
tgtcctctcc agaggtcatt tccttgggcc actggaggac tgtgagttct gagtcacact    2100
gtcagaccaa ggccaagggt gtttagaaac atctatggct gaggatcc                2148
```

<210> SEQ ID NO 4
<211> LENGTH: 1712
<212> TYPE: DNA
<213> ORGANISM: Mus musculus
<220> FEATURE:
<223> OTHER INFORMATION: Kir6.1 cDNA

<400> SEQUENCE: 4

```
cggcacaggt tctggaggac caacatcccc cggatctgca cttcggtgagg tctctgctcc    60 cgggatgcga gactgggacc agcccgccct gtgggctcaa gccgcagccg ggagcgcaaa   120
cccgagtctt ctaggaggac gcgtgtggag gaaaggagcc acaggttcag gcaggtgcat   180
aggcgggcta tggtgaaagg aagatgttgg ccaggaagag catcatcccg gaggagtatg   240
tgctggcgcg catcgcagcg gagaacctgc gcaaaccgcg catccgcgac cgtctcccca   300
aagcccgctt catcgccaag agcggagcct gcaacctggc acacaagaac atccgagagc   360
aaggtcgctt cctgcaggac atcttcacca ccttggtaga cctgaagtgg cgtcacacgc   420
tggtcatctt caccatgtcc ttcctctgca gctggctgct cttcgctatc atgtggtggc   480
tggtggcttt cgcccacggg gacatctatg cttacatgga gaaaggcacc atggagaaga   540
gtggcctgga gtccgctgtc tgtgtgacca atgtcaggtc attcacgtct gcgtttctct   600
tctccattga ggttcaagtg accattgggt tggagggag aatgatgact gaggaatgcc   660
ctctggccat cacggttttg attctgcaga acatcgtggg tctgatcatc aacgcagtca   720
tgttgggctg catcttcatg aagacggcgc aggcccacag aagggcagag acgctgattt   780
tcagccgcca tgctgtgatt gccgtccgca atggcaagct gtgcttcatg ttccgggtgg   840
gtgacctgag gaagagcatg atcattagcg cctcggtgcg catccaggtg gtcaagaaaa   900
ccacgacgcc agaaggggag gtggtgccta ttcatcagca ggacattcct gttgataatc   960
ccatcgagag caataatatc ttcctagtgg ccccattgat catctgccac gtgattgaca  1020
agcgtagccc cctgtatgat atctcagcaa ctgaccttgc caatcaagac ctggaggtca  1080
tagtgattct cgagggcgtg gtagaaacca caggcatcac cacacaagca cggacctcct  1140
acattgccga ggagatccag tggggacacc gcttcgtgtc aattgtgact gaggaggagg  1200
gcgtgtactc tgtggactat tccaaatttg gtaacacggt gagagtggct cgcgccaagat 1260 gcagtgcccg ggagctggat gagaagcctt ccatcctgat tcagaccctc caaaagagcg  1320
aactgtcgca ccagaattct ctgcggaagc gcaactccat gaggagaaac aactccatga  1380
ggagaaacaa ctccatcagg aggaataact cttccctcat ggtgcccaag gtgcagttca  1440
tgactccaga aggaaaccag tgtccatcag aatcatgagg gcaggatgac cggagacagt  1500
tacttgttga gtcctgatga ctgatagcc tgaacagtca ctgtgtcctg atgactgaga  1560
gacaatccgg agacagttca ttgagttccg atgatcaaaa tattgcactc atcaccagtt  1620
cagggctgga gcacagtatt cctatcctaa tgcactgaga aatattaata tttgagacat  1680
taaacttcct gtattaataa acaataacac ac                                  1712
```

<210> SEQ ID NO 5
<211> LENGTH: 1486
<212> TYPE: DNA
<213> ORGANISM: Mus musculus
<220> FEATURE:
<223> OTHER INFORMATION: Kir 6.2 cDNA -continued

```
<400> SEQUENCE: 5
aaggttggta caagcttagg gtaacctgag gtagagggtt tagtgagggg tactctacaa      60
agaggcccta ggccaagcca gtgtagtgcc tcccccatg gggaaaccc cttcccgggg       120 ccaacggagc catgctgtcc cgaaagggca ttatccctga ggaatatgtg ctgacccggc    180
tggcagagga ccctgcagag cccaggtacc gtactcgaga gaggagggcc cgcttcgtgt    240
ccaagaaagg caactgcaac gtcgcccaca agaacattcg agagcagggc cgcttcctgc    300
aggatgtgtt caccacgctg gtggacctca atggccaca cactctgctc attttcacca    360
tgtccttcct gtgcagctgg ctgctctttg ccatggtctg gtggctcatc gccttcgccc    420
acggtgacct ggcccccgga gagggcacca atgtgccctg cgtcacaagc atccactcct    480
tttcatctgc cttccttttc tccatcgagg tccaggtgac cattggtttc ggcgggcgca    540
tggtgacaga ggaatgtccc ctggccatcc tcattctcat tgtgcagaat atcgtcgggc    600
tgatgatcaa cgccatcatg ctgggctgca tcttcatgaa acggcccag gcccatcggc    660 gggcagaaac cctcatcttc agcaagcatg ctgtgatcac cctgcgccat ggccgcctgt    720
gcttcatgct gcgcgtaggg gacctccgaa agagcatgat cattagcgcc accatccaca    780
tgcaggtggt gcgcaagacc accagccccg agggcgaagt tgtgcctctc caccaggtag    840
acatccccat ggagaatggc gtgggtggta acggcatctt cctggtggcc ccactcatca    900
tctaccacgt catcgactcc aacagcccgc tctacgacct ggctcctagt gacctgcacc    960
accaccagga cctggagatc attgtcatct tggaaggcgt ggtagaaacc acgggcatca   1020
ccacccaggc ccgcacctcc tacctagctg acgagattct atgggggcag cgctttgtcc   1080
ccattgtggc cgaggaggac ggccgctatt ctgtggacta ctccaaattt ggtaacacca   1140
ttaaagtgcc cacaccactc tgcacagccc gccagcttga tgaggaccgc agtctgctgg   1200
atgccctgac cctcgcctcg tcgcgggggc cctgcgcaa gcgcagtgtg gctgtggcga   1260
aggccaagcc caagtttagc atctctccag attccttgtc ctgagttgca gttcctcagg   1320
cccccactca cttgtgtggg cacgtggaaa gtgaagtatg gtatgtagag tggtgggtg   1380 cgagcctctt ggccagacga gggtctggtg tgggacaaga ccctgctcgg ctcagcctcc   1440
ccgctgctgt gtgtctgggg tgttacaaga tacttgtcac tatgct                  1486
```

```
<210> SEQ ID NO 6
<211> LENGTH: 4826
<212> TYPE: DNA
<213> ORGANISM: Homo sapiens
<220> FEATURE:
<223> OTHER INFORMATION: SUR1 cDNA

<400> SEQUENCE: 6
agctgagccc gagcccagac cgcgcccgcg ccgccatgcc cctggccttc tgcggcagcg      60
agaaccactc ggccgcctac cggggtggacc aggggtcct caacaacggc tgctttgtgg    120
acgcgctcaa cgtggtgccg cacgtcttcc tactcttcat caccttcccc atcctcttca    180
ttggatgggg aagtcagagc tccaaggtgc acatccacca cagcacatgg cttcatttcc    240
ctgggcacaa cctgcggtgg atcctgacct tcatgctgct cttcgtcctg gtgtgtgaga    300
ttgcagaggg catcctgtct gatgggtga ccgaatccca ccatctgcac ctgtacatgc    360
cagccgggat ggcgttcatg gctgctgtca cctccgtggt ctactatcac aacatcgaga    420
cttccaactt cccccaagctg ctaattgccc tgctggtgta ttggacctg gccttcatca    480 ccaagaccat caagtttgtc aagttcttgg accacgccat cggcttctcg cagctacgct    540
```

-continued

| | |
|---|---|
| tctgcctcac agggctgctg gtgatcctct atgggatgct gctcctcgtg gaggtcaatg | 600 |
| tcatcagggt gaggagatac atcttcttca agacaccgag ggaggtgaag cctcccgagg | 660 |
| acctgcaaga cctgggggta cgcttcctgc agcccttcgt gaatctgctg tccaaaggca | 720 |
| cctactggtg gatgaacgcc ttcatcaaga ctgcccacaa gaagcccatc gacttgcgag | 780 |
| ccatcgggaa gctgcccatc gccatgaggg ccctcaccaa ctaccaacgg ctctgcgagg | 840 |
| cctttgacgc ccaggtgcgg aaggacattc agggcactca aggtgcccgg gccatctggc | 900 |
| aggcactcag ccatgccttc gggaggcgcc tggtcctcag cagcactttc cgcatcttgg | 960 |
| ccgacctgct gggcttcgcc gggccactgt gcatctttgg gatcgtggac caccttggga | 1020 |
| aggagaacga cgtcttccag cccaagacac aatttctcgg ggtttacttt gtctcatccc | 1080 |
| aagagttcct tgccaatgcc tacgtcttag ctgtgcttct gttccttgcc ctcctactgc | 1140 |
| aaaggacatt tctgcaagca tcctactatg tggccattga aactggaatt aacttgagag | 1200 |
| gagcaataca gaccaagatt tacaataaaa ttatgcacct gtccacctcc aacctgtcca | 1260 |
| tgggagaaat gactgctgga cagatctgta atctggttgc catcgacacc aatcagctca | 1320 |
| tgtggttttt cttcttgtgc ccaaacctct gggctatgcc agtacagatc attgtgggtg | 1380 |
| tgattctcct ctactacata ctcggagtca gtgccttaat tggagcagct gtcatcattc | 1440 |
| tactggctcc tgtccagtac ttcgtggcca ccaagctgtc tcaggcccag cggagcacac | 1500 |
| tggagtattc caatgagcgg ctgaagcaga ccaacgagat gctccgcggc atcaagctgc | 1560 |
| tgaagctgta cgcctgggag aacatcttcc gcacgcgggt ggagacgacc cgcaggaagg | 1620 |
| agatgaccag cctcagggcc tttgccatct atacctccat ctccattttc atgaacacgg | 1680 |
| ccatccccat tgcagctgtc ctcataactt cgtgggcca tgtcagcttc ttcaaagagg | 1740 |
| ccgacttctc gccctccgtg cctttgcct ccctctccct cttccatatc ttggtcacac | 1800 |
| cgctgttcct gctgtccagt gtggtccgat ctaccgtcaa agctctagtg agcgtgcaaa | 1860 |
| agctaagcga gttcctgtcc agtgcagaga tccgtgagga gcagtgtgcc ccccatgagc | 1920 |
| ccacacctca gggcccagcc agcaagtacc aggcggtgcc cctcagggtt gtgaaccgca | 1980 |
| agcgtccagc ccgggaggat tgtcggggcc tcaccggccc actgcagagc ctggtcccca | 2040 |
| gtgcagatgg cgatgctgac aactgctgtg tccagatcat ggaggctac ttcacgtgga | 2100 |
| ccccagatgg aatccccaca ctgtccaaca tcaccattcg tatcccccga ggccagctga | 2160 |
| ctatgatcgt ggggcaggtg ggctgcggca gtcctcgct ccttctagcc gcactggggg | 2220 |
| agatgcagaa ggtctcaggg gctgtcttct ggagcagcct tcctgacagc gagataggag | 2280 |
| aggaccccag cccagagcgg gagacagcga ccgacttgga tatcaggaag agaggccccg | 2340 |
| tggcctatgc ttcgcagaaa ccatggctgc taaatgccac tgtggaggag aacatcatct | 2400 |
| ttgagagtcc cttcaacaaa caacggtaca gatggtcat tgaagcctgc tctctgcagc | 2460 |
| cagacatcga catcctgccc catggagacc agacccagat tggggaacgg ggcatcaacc | 2520 |
| tgtctggtgg tcaacgccag cgaatcagtg tggcccgagc cctctaccag cacgccaacg | 2580 |
| ttgtcttctt ggatgacccc ttctcagctc tggatatcca tctgagtgac cacttaatgc | 2640 |
| aggccggcat ccttgagctg ctccgggacg acaagaggac agtggtctta gtgacccaca | 2700 |
| agctacagta cctgccccat gcagactgga tcattgccat gaaggatggc accatccaga | 2760 |
| gggagggtac cctcaaggac ttccagaggt ctgaatgcca gctctttgag cactggaaga | 2820 |
| ccctcatgaa ccgacaggac caagagctgg agaaggagac tgtcacagag agaaaagcca | 2880 |
| cagagccacc ccagggccta tctcgtgcca tgtcctcgag ggatggcctt ctgcaggatg | 2940 |

-continued

| | | | | |
|---|---|---|---|---|
| aggaagagga | ggaagaggag | gcagctgaga | gcgaggagga | tgacaacctg tcgtccatgc | 3000 |
| tgcaccagcg | tgctgagatc | ccatggcgag | cctgcgccaa | gtacctgtcc tccgccggca | 3060 |
| tcctgctcct | gtcgttgctg | gtcttctcac | agctgctcaa | gcacatggtc ctggtggcca | 3120 |
| tcgactactg | gctggccaag | tggaccgaca | gcgccctgac | cctgacccct gcagccagga | 3180 |
| actgctccct | cagccaggag | tgcaccctcg | accagactgt | ctatgccatg gtgttcacgg | 3240 |
| tgctctgcag | cctgggcatt | gtgctgtgcc | tcgtcacgtc | tgtcactgtg gagtggacag | 3300 |
| ggctgaaggt | ggccaagaga | ctgcaccgca | gcctgctaaa | ccggatcatc ctagccccca | 3360 |
| tgaggttttt | tgagaccacg | ccccttggga | gcatcctgaa | cagatttca tctgactgta | 3420 |
| acaccatcga | ccagcacatc | ccatccacgc | tggagtgcct | gagccgctcc accctgctct | 3480 |
| gtgtctcagc | cctggccgtc | atctcctatg | tcacacctgt | gttcctcgtg gccctcttgc | 3540 |
| ccctggccat | cgtgtgctac | ttcatccaga | agtacttccg | ggtggcgtcc agggacctgc | 3600 |
| agcagctgga | tgacaccacc | cagcttccac | ttctctcaca | ctttgccgaa accgtagaag | 3660 |
| gactcaccac | catccgggcc | ttcaggtatg | aggcccggtt | ccagcagaag cttctcgaat | 3720 |
| acacagactc | caacaacatt | gcttccctct | tcctcacagc | tgccaacaga tggctggaag | 3780 |
| tccgaatgga | gtacatcggt | gcatgtgtgg | tgctcatcgc | agcggtgacc tccatctcca | 3840 |
| actccctgca | cagggagctc | tctgctggcc | tggtgggcct | gggccttacc tacgccctaa | 3900 |
| tggtctccaa | ctacctcaac | tggatggtga | ggaacctggc | agacatggag ctccagctgg | 3960 |
| gggctgtgaa | gcgcatccat | gggctcctga | aaaccgaggc | agagagctac gagggctcc | 4020 |
| tggcaccatc | gctgatccca | agaactggc | cagaccaagg | gaagatccag atccagaacc | 4080 |
| tgagcgtgcg | ctacgacagc | tccctgaagc | cggtgctgaa | gcacgtcaat gccctcatct | 4140 |
| cccctggaca | gaagatcggg | atctgcggcc | gcaccggcag | tgggaagtcc tccttctctc | 4200 |
| ttgccttctt | ccgcatggtg | gacacgttcg | aagggcacat | catcattgat ggcattgaca | 4260 |
| tcgccaaaact | gccgctgcac | accctgcgct | cacgcctctc | catcatcctg caggaccccg | 4320 |
| tcctcttcag | cggcaccatc | cgatttaacc | tggaccctga | gaggaagtgc tcagatagca | 4380 |
| cactgtggga | ggccctggaa | atcgcccagc | tgaagctggt | ggtgaaggca ctgccaggag | 4440 |
| gcctcgatgc | catcatcaca | gaaggcgggg | agaatttcag | ccaggacag aggcagctgt | 4500 |
| tctgcctggc | ccgggccttc | gtgaggaaga | ccagcatctt | catcatggac gaggccacgg | 4560 |
| cttccattga | catggccacg | gaaaacatcc | tccaaaaggt | ggtgatgaca gccttcgcag | 4620 |
| accgcactgt | ggtcaccatc | gcgcatcgag | tgcacaccat | cctgagtgca gacctggtga | 4680 |
| tcgtcctgaa | gcggggtgcc | atccttgagt | tcgataagcc | agagaagctg ctcagccgga | 4740 |
| aggacagcgt | cttcgcctcc | ttcgtccgtg | cagacaagtg | acctgccaga gcccaagtgc | 4800 |
| catcccacat | tcggaccctg | cccata | | | 4826 |

<210> SEQ ID NO 7
<211> LENGTH: 5000
<212> TYPE: DNA
<213> ORGANISM: Rattus norvegicus
<220> FEATURE:
<223> OTHER INFORMATION: SUR2 cDNA

<400> SEQUENCE: 7

| | | | | |
|---|---|---|---|---|
| agcagctggc | ctcccaccac | cctaaaaata | atccactcgc | cgctgtctgc tgacccggga | 60 |
| ggaaaacttg | tcatcccatg | gagtgtgtga | gctcctcggc | ttgctccaga gagatcccca | 120 |
| accgctttga | ggagtcagtg | actgagttct | gtggacttgt | ttgaaattta catcttcaga | 180 |

```
ctgtgcgcag gcggttggaa ggtagatcaa gtgcaccagt agggggacta agttcctgag       240
ccaaagtcaa ggctaatcaa ctaagaagaa atgagccttt ccttctgtgg taacaacatc       300
tcctcctaca acatctacca tggtgttctc caaaacccct gctttgtgga cgcactcaac       360
ctggtccctc acgtcttcct gctgtttatc acctttccga tcctgttcat tggatggggg       420
agccaaagct caaaagtgca aattcatcac aacacatggc ttcatttttcc tggacacaac     480 ctgagatgga ttctgacgtt tgcactcctg tttgtgcatg tctgcgagat agcagaaggc       540
attgtttcag actcgcaacg ggcgtccagg catctccacc ttttcatgcc ggctgtgatg       600
ggatttgtcg ccaccaccac atccattgtg tattaccaca acattgaaac atcaaacttc       660
cctaaattac ttttagcttt attcctgtac tgggtcatgg ccttcattac aaagacaata       720
aagttggtca atactggca gttggggtgg ggaatgtcag acctgcgctt ctgcatcacg        780
ggagtgatgg tcatcttgaa tggactgctg atggctgtgg agatcaatgt catccgggtc      840
cgaagatatg ttttcttcat gaatcctcag aaagtgaagc ctccagagga cctccaggac      900
ctgggcgtga ggttcctcca gccgtttgtg aatttgctgt ccaaagctac ttactggtgg      960
atgaacacgc ttatcatatc agctcacagg aaacctattg atctgaaggc gatcggaaag     1020
ttgccgatag caatgagggc ggtgacgaat tatgtttgct tgaaggaggc ctacgaagag     1080
cagaagaaaa aggctgcgga tcatccgaat cggactccct ccatatggct ggccatgtac     1140
agggcttttg ggagaccgat cctgctgagc agcacgttcc gctacttggc tgacttgctg     1200
ggctttgccg gccctctttg tatttccgga atcgtccagc gtgtgaatga accgaagaat     1260
aacacgacga gattttcaga gacactctca tcaaaggagt ttctggaaaa tgcccatgtg     1320
ctggctgtcc tgctcttcct ggccctcatc ctgcaaagaa catttttgca ggcttcgtac     1380
tatgtgacca tagagaccgg catcaacctg cgtggggctc tgctggctat gatctacaac     1440
aaaatccttc gactgtctac ttctaaccta tccatgggcg agatgaccct gggacagatc     1500
aacaacttgg ttgccataga aaccaatcag ctcatgtggt tcttgttcct gtgtcccaat     1560
ctgtgggcca tgcccgttca gatcataatg ggggtgatcc tgctctataa tctgcttggg     1620
tcaagcgcac tggtaggcgc ggcggtcatc gtgctcctcg caccgattca gtacttcatc     1680
gccacgaagc tggcggaggc tcagaagagc actctggatt attccaccga gaggctgaag     1740
aagacaaacg agatactgaa aggcatcaag ctccttaagc tgtatgcctg ggagcacatt     1800
ttctgcaaga gcgtggaaga gactagaatg aaggagctct ccagcctcaa aaccttcgcg     1860
ctctacacgt cgcttttccat cttcatgaac gcagccattc ccatcgcagc cgttcttgca     1920
acatttgtga cccatgccta tgccagtggc aacaacctga accccgcaga ggcctttgcc     1980
tctctgtctc tcttccacat cctcgtcaca ccgctcttcc tgctgtccac ggtggtcaga     2040
ttcgcagtga agccatcat cagcgttcag aagctgaatg agtttctctt gagcgatgag     2100
attggcgagg acagctggag gactggggag gggacgctgc ttttgagtc ctgtaagaag     2160 cacaccggag tgcaatcaaa accgataaac aggaagcagc ctggaaggta ccacctggac     2220
aactacgagc aggcgcggcg tcttcggcct gctgagactg aagatgttgc cataaaggtg     2280
acgaacggat acttctcatg gggcagtggt ttagccacat tatccaatat tgacattcga     2340
attccaacag gtcagctaac catgattgtg ggtcaggtgg gttgtggcaa atcgtctctc     2400
ctccttgcca tccttggtga gatgcagacc ctggaaggaa agtttactg gaacaatgta     2460 aatgaatctg agccttcttt tgaagcaacc cgaagcagaa gcaggtactc tgtggcttat     2520
gctgcccaga agccttggct cctcaatgct acggtcgagg aaaacatcac ttttggaagt     2580
```

```
tctttcaaca gacagaggta caaggctgtc accgatgcct gctctctgca gccagacatt      2640
gatttgttac cctttggaga ccaaactgaa attggagaga ggggtatcaa cctgagtggg      2700
ggtcagaggc agagaatctg cgtggcccgg gcactctacc agaacaccaa tattgtcttc      2760
ttggacgatc cattctccgc tctggacatc cacctgagcg accacttgat gcaggaaggg      2820
atcctgaagt ttctccagga cgacaagagg acggtcgtcc ttgtgactca caaactacag      2880
tacctgacgc acgcggactg gatcatagcc atgaaggatg ggagtgtgtt aagggaaggg      2940
actttgaaag acatccagac caaagacgtg gagctctatg aacactggaa acccctcatg      3000
aatcggcaag atcaggaatt agaaaaggac atggaagccg accaaacaac gctggagagg      3060
aagactctcc gaagagctat gtactcaagg gaggccaaag cacagatgga ggatgaagat      3120
gaagaggagg aggaggagga agatgaggac gacaacatgt caactgtaat gaggctcagg      3180
acgaagatgc cctggaagac ctgttggtgg tacctcactt caggagggtt tttcctgctc      3240
ttcctcatga tcttctctaa gcttttgaag cactctgtga tcgtggccat cgactactgg      3300
ctagctacgt ggacctccga gtacagtata aacgacccag ggaaagctga ccagaccttc      3360
tatgtggctg ggttcagcat cctctgtgga gcgggcattt tcctttgcct cgtcacctcc      3420
ctcactgtag aatggatggg tctcaccgcc gccaagaacc tccaccacaa tctcctcaat      3480
aagataattc tgggcccaat aaggttcttt gataccacgc ccctgggact gatcctcaat      3540
cggttttctg ctgataccaa catcatcgac caacatatcc ctccgacctt ggagtcgctg      3600
acccgctcta ccctgctctg cctgtcggct attgggatga tctcctatgc tacacccgtg      3660
tttctcatcg ctcttgcgcc cctgggcgtc gccttttatt tcatccagaa atacttccgg      3720
gttgcctcta aggatctcca ggaactcgat gacagcaccc agctccccct gctttgtcac      3780
ttctcagaaa cagctgaagg gcttaccact atccgggcct caggcatga aaccagattc      3840 aagcaacgca tgctggagct gacagacaca aacaacattg cctacttatt tctctccgca      3900
gccaacagat ggctggaggt caggacggac tacctgggag cttgcattgt tctgacggcc      3960
tccattgcat ccatcagtgg ctcttccaac tctggactag tgggcttggg ccttctgtat      4020
gccctcacga taaccaatta cctgaattgg gttgtaagga acttggccga cctcgaagtc      4080
cagatgggcg cagtgaagaa agtgaacagt ttcttaacta tggagtctga gaactatgaa      4140
ggcaccatgg atccttctca gtcccagag cattggccac aggaaggtga gatcaagatt      4200
cacgatctat gcgtcagata tgaaaataac ctgaagcccg ttctgaaaca tgtcaaggct      4260
tacatcaagc ctgggcagaa ggtgggcatc tgtggtcgca ccggtagtgg gaagtcctct      4320
ctatctctgg ctttcttcag aatggtcgac atatttgatg aaagatagt cattgatgga      4380 atagacattt ccaagctgcc cttgcacacg ctccgctcta gactgtccat cattctccag      4440
gacccaatcc tgttcagcgg ctctatcaga tttaacttgg atcctgaatg caagtgcaca      4500
gacgacaggc tctgggaggc tctggaaatt gctcagttga agaatatggt caaatctctg      4560
ccaggaggcc tagacgccac tgtcaccgaa ggtggtgaga acttcagcgt tggacagaga      4620
cagctgttct gcctggccag ggcctttgtt cgaaagagca gcatactcat tatgatgag      4680 gccacggcct ccatcgacat ggccacggaa acatttgc agaaagtagt catgacagcc      4740
tttgcggatc gcacggttgt aaccatagct caccgtgtct cctctattat ggatgcgggc      4800
cttgttttag tcttttctga gggtatttta gtggagtgcg atactggtcc aaacctgctc      4860
cagcacaaga atggcctctt ttctactttg gtgatgacca acaagtagac cagcaagatc      4920
```

| | |
|---|---|
| tgctcctcca agtgtctcgt tctctgcatc gggttcacac cattctgact gctgacctgg | 4980 |
| tcattgtgat gaagagagga | 5000 |